US009862997B2

(12) United States Patent
Huber et al.

(10) Patent No.: US 9,862,997 B2
(45) Date of Patent: Jan. 9, 2018

(54) NANOPORE-BASED NUCLEIC ACID ANALYSIS WITH MIXED FRET DETECTION

(71) Applicant: Quantapore, Inc., Menlo Park, CA (US)

(72) Inventors: Martin Huber, Menlo Park, CA (US); Bason E. Clancy, Redwood City, CA (US); Paul Hardenbol, San Francisco, CA (US)

(73) Assignee: Quantapore, Inc., Menlo Park, CA (US)

( * ) Notice: Subject to any disclaimer, the term of this patent is extended or adjusted under 35 U.S.C. 154(b) by 153 days.

(21) Appl. No.: 14/786,518

(22) PCT Filed: May 23, 2014

(86) PCT No.: PCT/US2014/039444
§ 371 (c)(1),
(2) Date: Oct. 22, 2015

(87) PCT Pub. No.: WO2014/190322
PCT Pub. Date: Nov. 27, 2014

(65) Prior Publication Data
US 2016/0076091 A1    Mar. 17, 2016

Related U.S. Application Data

(60) Provisional application No. 61/827,519, filed on May 24, 2013.

(51) Int. Cl.
*C12Q 1/68* (2006.01)

(52) U.S. Cl.
CPC .................... *C12Q 1/6869* (2013.01)

(58) Field of Classification Search
None
See application file for complete search history.

(56) References Cited

U.S. PATENT DOCUMENTS

| 4,161,690 A | 7/1979 | Feier |
| 4,962,037 A | 10/1990 | Jett et al. |
| 5,131,755 A | 7/1992 | Chadwick et al. |

(Continued)

FOREIGN PATENT DOCUMENTS

| CN | 1403817 | 3/2003 |
| CN | 201302544 | 9/2009 |

(Continued)

OTHER PUBLICATIONS

US 8,008,014, 08/2011, Gershow et al. (withdrawn)

(Continued)

*Primary Examiner* — Betty J Forman
(74) *Attorney, Agent, or Firm* — Levine Bagade Han LLP

(57) ABSTRACT

Various methods, systems and devices for optical detection and analysis of polymers, such as polynucleotides, using nanopores, e.g., for determining sequences of nucleic acids, are provided herein. In certain variations, methods and systems for determining a nucleotide sequence of a polynucleotide, which include measuring mixed FRET signals as a polynucleotide translocates through a nanopore and determining a nucleotide sequence of the polynucleotide from the mixed FRET signals, are provided.

17 Claims, 7 Drawing Sheets

(56) References Cited

U.S. PATENT DOCUMENTS

| | | | |
|---|---|---|---|
| 5,356,776 | A | 10/1994 | Kambara et al. |
| 5,387,926 | A | 2/1995 | Bellan |
| 5,405,747 | A | 4/1995 | Jett et al. |
| 5,470,705 | A | 11/1995 | Grossman et al. |
| 5,580,732 | A | 12/1996 | Grossman et al. |
| 5,624,800 | A | 4/1997 | Grossman et al. |
| 5,624,845 | A * | 4/1997 | Wickramasinghe ... B82Y 20/00 250/311 |
| 5,795,782 | A | 8/1998 | Church et al. |
| 5,798,042 | A | 8/1998 | Chu et al. |
| 5,821,058 | A | 10/1998 | Smith et al. |
| 5,945,312 | A | 8/1999 | Goodman et al. |
| 5,989,871 | A | 11/1999 | Grossman et al. |
| 6,015,714 | A | 1/2000 | Baldarelli et al. |
| 6,136,543 | A | 10/2000 | Anazawa et al. |
| 6,210,896 | B1 | 4/2001 | Chan |
| 6,211,955 | B1 | 4/2001 | Basiji et al. |
| 6,249,341 | B1 | 6/2001 | Basiji et al. |
| 6,251,303 | B1 | 6/2001 | Bawendi et al. |
| 6,252,303 | B1 | 6/2001 | Huang |
| 6,263,286 | B1 | 7/2001 | Gilmanshin et al. |
| 6,267,872 | B1 | 7/2001 | Akeson et al. |
| 6,325,968 | B1 | 12/2001 | Fricker et al. |
| 6,335,420 | B1 | 1/2002 | Bruening et al. |
| 6,335,440 | B1 | 1/2002 | Lee et al. |
| 6,355,420 | B1 | 3/2002 | Chan |
| 6,362,002 | B1 | 3/2002 | Denison et al. |
| 6,413,792 | B1 | 7/2002 | Sauer et al. |
| 6,426,231 | B1 | 7/2002 | Bayley et al. |
| 6,428,959 | B1 | 8/2002 | Deamer |
| 6,429,897 | B2 | 8/2002 | Derndinger et al. |
| 6,447,724 | B1 | 9/2002 | Jensen et al. |
| 6,464,842 | B1 | 10/2002 | Golovchenko et al. |
| 6,465,193 | B2 | 10/2002 | Akeson et al. |
| 6,473,176 | B2 | 10/2002 | Basiji et al. |
| 6,498,010 | B1 | 12/2002 | Fitzgerald et al. |
| 6,503,757 | B1 | 1/2003 | Chow |
| 6,504,943 | B1 | 1/2003 | Sweatt et al. |
| 6,511,802 | B1 | 1/2003 | Albrecht et al. |
| 6,528,258 | B1 | 3/2003 | Russell |
| 6,537,755 | B1 | 3/2003 | Drmanac |
| 6,583,865 | B2 | 6/2003 | Basiji et al. |
| 6,608,680 | B2 | 8/2003 | Basiji et al. |
| 6,608,682 | B2 | 8/2003 | Ortyn et al. |
| 6,616,895 | B2 | 9/2003 | Dugas et al. |
| 6,617,113 | B2 | 9/2003 | Deamer |
| 6,618,140 | B2 | 9/2003 | Frost et al. |
| 6,618,679 | B2 | 9/2003 | Loehrlein et al. |
| 6,627,067 | B1 | 9/2003 | Branton et al. |
| 6,671,044 | B2 | 12/2003 | Ortyn et al. |
| 6,673,615 | B2 | 1/2004 | Denison et al. |
| 6,706,203 | B2 | 3/2004 | Barth et al. |
| 6,723,515 | B2 | 4/2004 | Barron |
| 6,743,905 | B2 | 6/2004 | Woo et al. |
| 6,746,594 | B2 | 6/2004 | Akeson et al. |
| 6,752,914 | B1 | 6/2004 | Hassard |
| 6,756,204 | B2 | 6/2004 | Grossman et al. |
| 6,758,961 | B1 | 7/2004 | Vogel et al. |
| 6,772,070 | B2 | 8/2004 | Gilmanshin et al. |
| 6,790,671 | B1 | 9/2004 | Austin et al. |
| 6,821,726 | B1 | 11/2004 | Dahm et al. |
| 6,824,659 | B2 | 11/2004 | Bayley et al. |
| 6,830,670 | B1 | 12/2004 | Viovy et al. |
| 6,855,551 | B2 | 2/2005 | Bawendi et al. |
| 6,856,390 | B2 | 2/2005 | Nordman et al. |
| 6,906,749 | B1 | 6/2005 | Fox |
| 6,916,665 | B2 | 7/2005 | Bayley et al. |
| 6,936,433 | B2 | 8/2005 | Akeson et al. |
| 6,947,128 | B2 | 9/2005 | Basiji et al. |
| 6,952,651 | B2 | 10/2005 | Su |
| 6,975,400 | B2 | 12/2005 | Ortyn et al. |
| 6,982,146 | B1 | 1/2006 | Schneider et al. |
| 6,998,251 | B2 | 2/2006 | Guttman et al. |
| 7,001,792 | B2 | 2/2006 | Sauer et al. |
| 7,005,264 | B2 | 2/2006 | Su et al. |
| 7,008,547 | B2 | 3/2006 | Chen et al. |
| 7,049,104 | B2 | 5/2006 | Kambara et al. |
| 7,052,847 | B2 | 5/2006 | Korlach et al. |
| 7,056,661 | B2 | 6/2006 | Korlach et al. |
| 7,056,676 | B2 | 6/2006 | Korlach et al. |
| 7,060,507 | B2 | 6/2006 | Akeson et al. |
| 7,074,569 | B2 | 7/2006 | Woo et al. |
| 7,129,050 | B2 | 10/2006 | Grossman et al. |
| 7,189,503 | B2 | 3/2007 | Akeson et al. |
| 7,201,836 | B2 | 4/2007 | Vogel et al. |
| 7,235,184 | B2 | 6/2007 | Dugas et al. |
| 7,235,361 | B2 | 6/2007 | Bawendi et al. |
| 7,238,485 | B2 | 7/2007 | Akeson et al. |
| 7,244,349 | B2 | 7/2007 | Vogel et al. |
| 7,248,771 | B2 | 7/2007 | Schmidt et al. |
| 7,250,115 | B2 | 7/2007 | Barth |
| 7,271,896 | B2 | 9/2007 | Chan et al. |
| 7,279,337 | B2 | 10/2007 | Zhu |
| 7,280,207 | B2 | 10/2007 | Oldham et al. |
| 7,285,010 | B2 | 10/2007 | Hatakeyama et al. |
| 7,364,851 | B2 | 4/2008 | Berlin et al. |
| 7,371,533 | B2 | 5/2008 | Slater et al. |
| 7,381,315 | B2 | 6/2008 | Grossman et al. |
| 7,387,715 | B2 | 6/2008 | Vogel et al. |
| 7,390,457 | B2 | 6/2008 | Schembri |
| 7,397,232 | B2 | 7/2008 | Hu et al. |
| 7,410,564 | B2 | 8/2008 | Flory |
| 7,428,047 | B2 | 9/2008 | Oldham et al. |
| 7,438,193 | B2 | 10/2008 | Yang et al. |
| 7,444,053 | B2 | 10/2008 | Schmidt et al. |
| 7,468,271 | B2 | 12/2008 | Golovchenko et al. |
| 7,476,503 | B2 | 1/2009 | Turner et al. |
| 7,553,730 | B2 | 6/2009 | Barth et al. |
| 7,567,695 | B2 | 7/2009 | Frost et al. |
| 7,595,023 | B2 | 9/2009 | Lewis et al. |
| 7,609,309 | B2 | 10/2009 | Brown et al. |
| 7,622,934 | B2 | 11/2009 | Hibbs et al. |
| 7,625,706 | B2 | 12/2009 | Akeson et al. |
| 7,651,599 | B2 | 1/2010 | Blaga et al. |
| 7,666,593 | B2 | 2/2010 | Lapidus |
| 7,670,770 | B2 | 3/2010 | Chou et al. |
| 7,678,562 | B2 | 3/2010 | Ling |
| 7,744,816 | B2 | 6/2010 | Su et al. |
| 7,777,505 | B2 | 8/2010 | White et al. |
| 7,803,607 | B2 | 9/2010 | Branton et al. |
| 7,835,870 | B2 | 11/2010 | Nair et al. |
| 7,838,873 | B2 | 11/2010 | Clevenger et al. |
| 7,843,562 | B2 | 11/2010 | Chan et al. |
| 7,846,738 | B2 | 12/2010 | Golovchenko et al. |
| 7,849,581 | B2 | 12/2010 | White et al. |
| 7,871,777 | B2 | 1/2011 | Schneider et al. |
| 7,883,869 | B2 | 2/2011 | Ju et al. |
| 7,897,338 | B2 | 3/2011 | Woo et al. |
| 7,947,454 | B2 | 5/2011 | Akeson et al. |
| 7,972,858 | B2 | 7/2011 | Meller et al. |
| 8,105,846 | B2 | 1/2012 | Bayley et al. |
| 8,206,568 | B2 | 6/2012 | Branton et al. |
| 8,394,584 | B2 | 3/2013 | Timp et al. |
| 8,394,640 | B2 | 3/2013 | Golovchenko et al. |
| 8,435,775 | B2 | 5/2013 | Holliger et al. |
| 8,440,403 | B2 | 5/2013 | Frayling |
| 8,771,491 | B2 * | 7/2014 | Huber ............... C12Q 1/6869 204/452 |
| 8,802,838 | B2 | 8/2014 | Meller et al. |
| 8,865,078 | B2 | 10/2014 | Chiou et al. |
| 8,865,455 | B2 | 10/2014 | Frayling |
| 9,121,843 | B2 | 9/2015 | Meller et al. |
| 9,279,153 | B2 * | 3/2016 | Huber ............... C12Q 1/6869 |
| 2002/0034762 | A1 | 3/2002 | Muller et al. |
| 2002/0119455 | A1 | 8/2002 | Chan |
| 2003/0003463 | A1 | 1/2003 | Rothberg et al. |
| 2003/0064366 | A1 | 4/2003 | Hardin et al. |
| 2003/0092005 | A1 | 5/2003 | Levene et al. |
| 2003/0096220 | A1 | 5/2003 | Lafferty et al. |
| 2003/0143614 | A1 | 7/2003 | Drmanac |
| 2003/0148544 | A1 | 8/2003 | Nie et al. |
| 2003/0174992 | A1 | 9/2003 | Levene et al. |
| 2003/0207326 | A1 | 11/2003 | Su et al. |
| 2003/0215881 | A1 | 11/2003 | Bayley et al. |

(56) References Cited

U.S. PATENT DOCUMENTS

| | | |
|---|---|---|
| 2004/0002089 A1 | 1/2004 | Dubertret et al. |
| 2004/0033492 A1 | 2/2004 | Chen |
| 2004/0137158 A1 | 7/2004 | Kools et al. |
| 2004/0146430 A1 | 7/2004 | Dugas |
| 2004/0175710 A1 | 9/2004 | Haushalter |
| 2004/0214221 A1 | 10/2004 | Muehlegger et al. |
| 2005/0014154 A1 | 1/2005 | Weizenegger |
| 2005/0019784 A1 | 1/2005 | Su et al. |
| 2005/0095599 A1 | 5/2005 | Pittaro et al. |
| 2005/0130159 A1 | 6/2005 | Rigler et al. |
| 2005/0130173 A1 | 6/2005 | Leamon et al. |
| 2005/0136408 A1 | 6/2005 | Tom et al. |
| 2005/0147992 A1 | 7/2005 | Quake et al. |
| 2005/0153284 A1 | 7/2005 | Foldes et al. |
| 2005/0164211 A1 | 7/2005 | Hannah |
| 2005/0186576 A1 | 8/2005 | Chan et al. |
| 2005/0186629 A1 | 8/2005 | Barth |
| 2005/0196876 A1 | 9/2005 | Chan et al. |
| 2005/0227239 A1 | 10/2005 | Joyce |
| 2005/0241933 A1 | 11/2005 | Branton et al. |
| 2005/0282229 A1 | 12/2005 | Su et al. |
| 2006/0003458 A1 | 1/2006 | Golovchenko et al. |
| 2006/0019247 A1 | 1/2006 | Su et al. |
| 2006/0019259 A1 | 1/2006 | Joyce |
| 2006/0063171 A1 | 3/2006 | Akeson et al. |
| 2006/0147942 A1 | 7/2006 | Buzby |
| 2006/0210995 A1 | 9/2006 | Joyce |
| 2006/0231419 A1 | 10/2006 | Barth et al. |
| 2006/0251371 A1 | 11/2006 | Schmidt et al. |
| 2006/0292041 A1 | 12/2006 | Dugas et al. |
| 2007/0012865 A1 | 1/2007 | Katzir et al. |
| 2007/0037199 A1 | 2/2007 | Takahashi et al. |
| 2007/0042366 A1 | 2/2007 | Ling |
| 2007/0054276 A1 | 3/2007 | Sampson |
| 2007/0172858 A1 | 7/2007 | Hardin et al. |
| 2007/0172865 A1 | 7/2007 | Hardin et al. |
| 2007/0190542 A1 | 8/2007 | Ling et al. |
| 2007/0190543 A1 | 8/2007 | Livak |
| 2007/0202008 A1 | 8/2007 | Schembri et al. |
| 2007/0215472 A1 | 9/2007 | Slater et al. |
| 2007/0218494 A1 | 9/2007 | Slater et al. |
| 2007/0224613 A1 | 9/2007 | Strathmann |
| 2007/0231795 A1 | 10/2007 | Su |
| 2007/0264623 A1 | 11/2007 | Wang et al. |
| 2008/0025875 A1 | 1/2008 | Martin et al. |
| 2008/0032290 A1 | 2/2008 | Young |
| 2008/0050752 A1 | 2/2008 | Sun et al. |
| 2008/0187915 A1 | 8/2008 | Polonsky et al. |
| 2008/0193956 A1 | 8/2008 | Kricka et al. |
| 2008/0218184 A1 | 9/2008 | White et al. |
| 2008/0254995 A1 | 10/2008 | Kim et al. |
| 2008/0261204 A1 | 10/2008 | Lexow |
| 2008/0274905 A1 | 11/2008 | Greene |
| 2008/0311375 A1 | 12/2008 | Harnack et al. |
| 2009/0021735 A1 | 1/2009 | Oldham et al. |
| 2009/0024331 A1 | 1/2009 | Tomaney et al. |
| 2009/0029477 A1 | 1/2009 | Meller et al. |
| 2009/0035777 A1 | 2/2009 | Kokoris et al. |
| 2009/0061447 A1 | 3/2009 | Schneider |
| 2009/0066315 A1 | 3/2009 | Hu et al. |
| 2009/0136958 A1 | 5/2009 | Gershow et al. |
| 2009/0137007 A1 | 5/2009 | Korlach et al. |
| 2009/0148348 A1 | 6/2009 | Pettigrew et al. |
| 2009/0185955 A1 | 7/2009 | Nellissen |
| 2009/0222216 A1 | 9/2009 | Hibbs et al. |
| 2009/0250615 A1 | 10/2009 | Oldham et al. |
| 2009/0277869 A1 | 11/2009 | Dugas |
| 2009/0298075 A1 | 12/2009 | Travers et al. |
| 2009/0305278 A1 | 12/2009 | Hardin et al. |
| 2009/0314939 A1 | 12/2009 | Stern et al. |
| 2010/0025249 A1 | 2/2010 | Polonsky et al. |
| 2010/0029508 A1 | 2/2010 | Austin et al. |
| 2010/0035260 A1 | 2/2010 | Olasagasti et al. |
| 2010/0035268 A1 | 2/2010 | Beechem et al. |
| 2010/0075309 A1 | 3/2010 | Maxham et al. |
| 2010/0103416 A1 | 4/2010 | Oldham et al. |
| 2010/0227913 A1 | 9/2010 | Lyakhov et al. |
| 2010/0262379 A1 | 10/2010 | Frazier |
| 2010/0292101 A1 | 11/2010 | So |
| 2010/0331194 A1 | 12/2010 | Turner et al. |
| 2011/0053284 A1 | 3/2011 | Meller et al. |
| 2011/0165652 A1* | 7/2011 | Hardin .................. C07H 19/10 435/194 |
| 2011/0172404 A1 | 7/2011 | Luo et al. |
| 2011/0177498 A1 | 7/2011 | Clarke et al. |
| 2011/0177978 A1 | 7/2011 | Luo et al. |
| 2011/0257043 A1 | 10/2011 | Meller et al. |
| 2011/0308950 A1 | 12/2011 | Sakai et al. |
| 2012/0055792 A1 | 3/2012 | Gundlach et al. |
| 2012/0135410 A1 | 5/2012 | Soni et al. |
| 2012/0199482 A1 | 8/2012 | Meller et al. |
| 2012/0261261 A1 | 10/2012 | Huber |
| 2013/0040827 A1 | 2/2013 | Macevicz |
| 2013/0176563 A1 | 7/2013 | Ozawa et al. |
| 2013/0203050 A1 | 8/2013 | Huber et al. |
| 2013/0203610 A1 | 8/2013 | Meller et al. |
| 2013/0256118 A1 | 10/2013 | Meller et al. |
| 2014/0087474 A1 | 3/2014 | Huber |
| 2014/0255935 A1 | 9/2014 | Huber |
| 2014/0367259 A1 | 12/2014 | Frayling et al. |
| 2015/0204840 A1 | 7/2015 | Soares et al. |

FOREIGN PATENT DOCUMENTS

| | | |
|---|---|---|
| EP | 1682673 | 7/2006 |
| WO | WO 2001/018247 | 3/2001 |
| WO | WO 2005/045392 | 5/2005 |
| WO | WO 2006/052882 | 5/2006 |
| WO | WO 2008/049795 | 5/2008 |
| WO | WO 2009/020682 | 8/2008 |
| WO | WO 2009/092035 | 1/2009 |
| WO | WO 2010/002883 | 2/2009 |
| WO | WO 2009/056831 | 5/2009 |
| WO | WO 2011/050147 | 7/2009 |
| WO | WO 2009/007743 | 1/2010 |
| WO | WO 2012/170499 | 1/2010 |
| WO | WO 2010/116595 | 10/2010 |
| WO | WO-11-040996 A1 * | 4/2011 |
| WO | WO 2011/040996 | 4/2011 |
| WO | WO 2011/067559 | 4/2011 |
| WO | WO 2008/092760 | 6/2011 |
| WO | WO 2012/121756 | 9/2012 |
| WO | WO 2010/007537 | 12/2012 |
| WO | WO 2014/066902 | 5/2014 |
| WO | WO 2014/066905 | 5/2014 |
| WO | WO 2014/190322 | 11/2014 |

OTHER PUBLICATIONS

Anderson, J. et al. "Incorporation of reporter-labeled nucleotides by DNA polymerases," *Biotechniques*, 38(2): 257-263, Feb. 2005.

Luan et al., "Slowing and controlling the translocation of DNA in a solid-state nanopore," *Nanoscale*, 4(4): 1068-1077, Feb. 21, 2012.

Roy et al. "A practical guide to single molecule FRET," *Nature Methods*, 5(6): 507-516, Jun. 2008.

Smolina, I.V. et al. "High-density fluorescently labeled rolling-circle amplicons for DNA diagnostics," *Analytical Biochemistry*, 347: 152-155, Jun. 21, 2005.

Timp, W., et al, "DNA base-calling form a nanopore using a Viterbi algorithm," *Biophysical J.*, vol. 102, pp. L37-L39, May 2012.

Aksimentiev, A. et al., "Microscopic Kinetics of DNA Translocation through Synthetic Nanopores," *Biophysical Journal*, vol. 87, pp. 2086-2097, Sep. 2004.

Algar, W. R. et al. "Quantum dots as donors in fluorescence resonance energy transfer for the bioanalysis of nucleic acids, proteins, and other biological molecules," *Anal Bioanal Chem*, vol. 391, abstract only, 2008.

Anderson, B.N. et al. "Probing Solid-State Nanopores with Light for the Detection of Unlabeled Analytes," *ACS Nano*, 8(11), pp. 11836-11845, Nov. 2014.

Anderson, M. et al, "Next Generation DNA Sequencing and the Future of Genomic Medicine," *Genes*, vol. 1, pp. 38-69, 2010.

(56) References Cited

OTHER PUBLICATIONS

Augustin, M.A. et al. "Progress towards single-molecule sequencing: enzymatic synthesis of nucleotide-specifically labeled DNA," *Journal of Biotechnology*, 86(3), pp. 289-301, Apr. 2001.

Australian Patent Application No. 2010301128 filed May 13, 2010 in the name of Huber, Office Action dated Aug. 15, 2014.

Baker, L.A. et al., "A makeover for membranes," *Nature Nanotechnology*, vol. 3, pp. 73-74, Feb. 2008.

Bayley, "Sequencing single molecules of DNA," *Current Opinion in Chemical Biology*,10(6), abstract only, Dec. 2006.

Begovich, A.B. et al., "A Missense Single-Nucleotide Polymorphism in a Gene Encoding a Protein Tyrosine Phosphatase (PTPN22) is Associated with Rheumatoid Arthritis," *The American Journal of Human Genetics*, vol. 75, No. 2, pp. 330-337, Aug. 1, 2004.

Brakmann, S. "High-Density Labeling of DNA for Single Molecule Sequencing," *Methods in Molecular Biology*, vol. 283, pp. 137-144, Jun. 2004.

Brakmann, S. et al. "High-Density Labeling of DNA: Preparation and Characterization of the Target Material for Single-Molecule Sequencing," *Angew. Chem. Int. Ed.*, 40(8), pp. 1427-1429, Apr. 2001.

Branton, D. et al, "The potential and challenges of nanopore sequencing," *Nature Biotechnology*, 26(10), pp. 1146-1153, Oct. 2008.

Butler, T. Z. et al., "Single-molecule DNA detection with an engineered MspA protein nanopore," *Proceedings of the National Academy of Sciences*, 105(52), pp. 20647-20652, Dec. 30, 2008.

Chan, E. Y. et al. "DNA Mapping Using Microfluidic Stretching and Single-Molecule Detection of Fluorescent Site-Specific Tags," *Genome Research*, vol. 14, pp. 1137-1146, 2004.

Chan, W.C. et al. "Quantum Dot Bioconjugates for Ultrasensitive Nonisotopic Detection," *Science*, vol. 281, pp. 2016-2018, Sep. 25, 1998.

Chansin, et al. "Single-Molecule Spactroscopy Using Nanoporous Membranes," *Nano Letters*,vol. 7, No. 9; pp. 2901-2906, 2007.

Chen, P. et al, "Atomic Layer Deposition to Fine-Tune the Surface Properties and Diameters of Fabricated Nanopores," *Nano Letters*, 4(7), pp. 1333-1337, 2004.

Cherf, G. et al, "Automated forward and reverse ratcheting of DNA in a nanopore at 5-A precision," *Nat Biotechnol.*, 30(4), 6 pages, Feb. 14, 2012.

Clarke, J. et al, "Continuous base identification for single-molecule nanopore DNA sequencing," *Nature Nanotechnology*, 4(4), pp. 265-270, Apr. 2009.

Danelon, C. et al. "Fabrication and Functionalization of Nanochannels by Electron-Beam-Induced Silicon Oxide Deposition," *Langmuir*, vol. 22, pp. 10711-10715, 2006.

Deamer, et al., "Characterization of Nucleic Acids by Nanopore Analysis," *Acc. Chem. Res.*, 35(10), pp. 817-825, 2002.

Deamer, et al., "Nanopores and nucleic acids: prospects for ultrarapid sequencing," *Trends in Biotechnology*, 18(4), abstract only (2 pages), Apr. 1, 2000.

Deblois, R. et al, "Counting and Sizing of Submicron Particles by the Resistive Pulse Technique," *Rev. Sci. Instruments*, 41(7), pp. 909-916, Jul. 1970.

Dekker, C. "Solid-state nanopores," *Nature Nanotechnology*, vol. 2, pp. 209-215, Apr. 2007.

Dela Torre, R. et al. "Fabrication and Characterization of Solid-state Nanopore Arrays for High Throughput DNA Sequencing," *Nanotechnology*,23(38), 12 pages, Sep. 28, 2012.

Dennis, A.M. et al., "Quantum Dot—Fluorescent Protein Pairs as Novel Fluorescence Resonance Energy Transfer Probes," *Nano Lett.*, vol. 8, No. 5, pp. 1439-1445, 2008, American Chemical Society.

Dorre, K. et al. "Highly efficient single molecule detection in microstructures," *Journal of Biotechnology*, 86(3), pp. 225-236, Apr. 2001.

Eid et al, "Real-time DNA sequencing from single polymerase molecules," *Science*, 232: 133-138, Jan. 2, 2009 and Supplemental Material.

Eigen, M. et al. "Sorting single molecules: Application to diagnostics and evolutionary biotechnology," *Proc. Natl. Acad. Sci.*, vol. 91, pp. 5740-5747, Jun. 1994.

Etoh, et al. "An Image Sensor Which Captures 100 Consecutive Frames at 1000000 Frames/s," *IEEE Transactions on Electron Devices*,vol. 50. No. 1; pp. 144-151, Jan. 2003.

European Patent Application No. 10820963.6 filed May 13, 2010 in the name of Huber, Search Report and Opinion dated Dec. 3, 2013.

Foldes-Papp, Z. et al. "Fluorescent high-density labeling of DNA: error-free substitution for a normal nucleotide," *Journal of Biotechnology*, 86(3), pp. 237-253, Mar. 2001.

Fologea, et al. "Detecting Single Stranded DNA with a Solid State Nanopore," *Nano Letters*, 5 (10), abstract only, Aug. 31, 2005.

Fontes, A. et al. "Quantum Dots in Biomedical Research," Biomedical Engineering—Technical Applications in Medicine, Chapter 12, pp. 269-290, Sep. 6, 2012.

Freeman, J. et al, "Profiling the T-cell receptor beta-chain repertoire by massively parallel sequencing," Genome Research, vol. 19, pp. 1817-1824, Jun. 2009.

Galla et al. "Microfluidic carbon-blackened polydimethylsiloxane device with reduced ultra violet 1-4 background fluorescence for simultaneous two-color ultra violetivisible-laser induced fluorescence detection in single cell analysis," *Biomicrofluidics* 6, pp. 014104-1 to 014104-10, Jan. 12, 2012.

Gierlich, J. et al, "Synthesis of Highly Modified DNA by a Combination of PCR with Alkyne-Bearing Triphosphates and Click Chemistry," *Chem. Eur. J.*, vol. 13, pp. 9486-9494, 2007.

Giller, G. et al. "Incorporation of reporter molecule-labeled nucleotides by DNA polymerases. I. Chemical synthesis of various reporter group-labeled 2'-deoxyribonucleoside-5'-triphosphates," *Nucleic Acids Research*, 31(10), pp. 2630-2635, May 2003.

Grayson, A. et al, "A BioMEMS Review: MEMS Technology for Physiologically Integrated Devices," *Proceedings IEEE*, 92(1), pp. 6-21, Jan. 2004.

Gu, L. et al, "Single molecule sensing by nanopores and nanopore devices," *Analyst*,135(3), pp. 441-451, 2010.

Gupta, et al., "Single-molecule DNA sequencing technologies for future genomic research," *Trends in Biotechnology*, 26(11), pp. 602-611, Nov. 1, 2008.

Ha, T. et al., "Probing the interaction between two single molecules: fluorescence resonance energy transfer between a single donor and a single acceptor," *Proc. Natl. Acad. Sci USA*, vol. 93, No. 13, pp. 6264-6268, Jun. 25, 1996.

Hagan, B. "Sequencing single Molecules of DNA," *Current Opinion in Chemical Biology*, vol. 10, Isssue 6, pp. 628-637, 2006.

Hall, A. R. et al. "Hybrid pore formation by directed insertion of alpha hemolysin into solid-state nanopores," *Nature Nanotechnology*, 5(12), pp. 874-877, Dec. 2010.

He, H. et al., "Single Nonblinking CdTe Quantum Dots Synthesized in Aqueous Thiopropionic Acid," *Angew. Chem. Int. Ed.* vol. 45, pp. 7588-7591, Oct. 2006.

Heins, E.A. et al., "Detecting Single Porphyrin Molecules in a Conically Shaped Synthetic Nanopore," *Nano Letters*, 5(9), pp. 1824-1829, Jul. 26, 2005.

Heins, E.A. et al., "Detecting Single Porphyrin Molecules in a Conically Shaped Synthetic Nanopore," *Nano Letters*, 5(9), pp. 1824-1829, Jul. 26, 2005, Supporting Information.

Heintzmann, R. et al., "Breaking the resolution limit in light microscopy," *Briefings in Functional Genomics and Proteomics*, 5(4), pp. 289-301, Dec. 2006.

Hemminger, "Visualizing and Understanding Complex MicroINanonuidic Flow Behavior," Dissertation, The Ohio State University, 2010, available online at <http://etd.ohiolink.edulsend•pdf.cgUHemminger%200rin%20L.pdf?osu1275398565>.

Henriquez, R. et al, "The resurgence of Coulter counting for analyzing nanoscale objects," *The Analyst*, 129, pp. 478-482, 2004.

Hlawacek, G. "Helium Ion Microscopy," *Journal of Vacuum Sciences B*, 32:020801, 16 pages, Feb. 6, 2014.

(56) References Cited

OTHER PUBLICATIONS

Hoevel, T. et al., "Cisplatin-Digoxigenin mRNA labeling for non-radioactive detection of mRNA hybridized onto nucleic acid cDNA arrays," *Biotechniques*, vol. 27, No. 5, pp. 1064-1067, Nov. 1999.
Holt, R. et al, "The new paradigm of flow cell sequencing," *Genome Research*, vol. 18, pp. 839-846, 2008.
Hsieh et al. "Effective Enhancement of Fluorescence Detection Efficiency in Protein MlcroarrayAssays: Application of a Highly AuorInated Organosllane as the Blocking Agent on the Background Surface by a Facile Vapor-Phase Deposition Process," *Anal. Chem.*, 88:7908-7916, 2009.
Huang, S. et al. "High-throughput optical sensing of nucleic acids in a nanopore array," *Nature Nanotechnology*, vol. 10, pp. 986-991, Aug. 2015.
Iqbal, S. M. et al., "Solid-state nanopore channels with DNA selectivity," *Nature Nanotechnology*, pp. 1-6, Apr. 1, 2007.
Ito, T. et al., "Observation of DNA transport through a single carbon nanotube channel using fluorescence microscopy," *Chem. Commun*, vol. 12, pp. 1482-1483, 2003.
Ivankin, A. et al. "Label-Free Optical Detection of Biomolecular Translocation through Nanopore Arrays," *ACS Nano*, 8(10), pp. 10774-10781, Sep. 2014.
Jagtiani, A. et al, "A label-free high throughput resistive-pulse sensor for simultaneous differentiation and measurement of multiple particle-laden analytes," *J. Micromech. Microeng.*, 16, pp. 1530-1539, 2006.
Japanese Patent Application No. 2012-532069 filed May 13, 2010 in the name of Huber, Final Office Action dated Apr. 17, 2015.
Japanese Patent Application No. 2012-532069 filed May 13, 2010 in the name of Huber, Office Action dated Aug. 1, 2014.
Japanese Patent Application No. 2014-224165 filed May 13, 2010 in the name of Huber, Office Action dated Oct. 15, 2015.
Johansson, MK et al. "Choosing Reporter-Quencher Pairs for Efficient Quenching Through Formation of Intramolecular Dimers," *Methods in Molecular Biology*, vol. 335:2, pp. 17-29, 2006.
Johansson, MK et al. "Intramolecular Dimers: A New Design Strategy for Fluorescence-Quenched Probes," *Chem. Eur. J.*, 9, 3466-3471, Jul. 2003.
Kang, X. et al., "A storable encapsulated bilayer chip containing a single protein nanopore," *J Am Chem Soc.* vol. 129, No. 15, pp. 4701-4705, Mar. 22, 2007.
Kasianowicz, J.J. et al., "Characterization of Individual Polynucleotide Molecules Using a Membrane Channel," *Proc. Natl. Acad. Sci USA*, vol. 93, pp. 13770-13773, Nov. 1996.
Keyser, U. F. "Controlling molecular transport through nanopores," *Journal of the Royal Society Interface*, 10 page, published online 2011.
Kircher, M. et al, "High-throughput DNA sequencing-concepts and limitations," *Bioessays*, vol. 32, pp. 524-536, 2010.
Kleefen, A. et al. "Multiplexed Parallel Single Transport Recordings on Nanopore Arrays," *Nano Letters*, vol. 10, pp. 5080-5087, 2010.
Kocer, A. et al. "Nanopore sensors: From hybrid to abiotic systems," *Biosensors and Bioelectronics*, vol. 38, 10 pages, 2012.
Kolb, H. et al, "Click Chemistry: Diverse Chemical Function from a Few Good Reactions," *Angew. Chem. Int. Ed.*, vol. 40, pp. 2005-2021, 2001.
Kristensen, V. N. et al., "High-Throughput Methods for Detection of Genetic Variation," *BioTechniques*, 30(2), pp. 318-332, Feb. 2001.
Lee et al. "High aspect ratio polymer microstructures and cantilevers for bIoMEMS using low energy ion beam and photolithography," *Sensors and Actuators A*, 71:144-149, Apr. 1998.
Lerner, H. et al, "Prospects for the Use of Next-Generation Sequencing Methods in Ornithology," *The Auk*, 127(1), pp. 4-15, 2010.
Levene et al, "Zero mode waveguide for single-molecule analysis in high concentration," *Science*, 299: 682-686, Jan. 31, 2003.
Li et al., "DNA Molecules and Configurations in a Solid-State Nanopore Microscope," *Nat. Mater*, vol. 2, pp. 611-615, Sep. 2003.
Li, J. et al., "Nanoscale Ion Beam Sculpting," *Nature*, vol. 412, 11 pages, Jul. 12, 2001.
Lin, B. et al., "Recent Patents and Advances in the Next-Generation Sequencing Technologies," *Recent Patents on Biomedical Engineering*, vol. 1, No. 1, pp. 60-67, 2008, Benthan Science Publishers Ltd.
Lo, C.J. et al., "Fabrication of symmetric sub-5 nm nanopores using focused ion and electron beams," *Nanotechnology*, vol. 17, No. 13, pp. 3264-3267, Jul. 2006.
Lu et al. "Parylene Background Fluorescence Study for Biomems Applications," *Transducers*, pp. 176-179, Jun. 21-25, 2009.
Maitra, R. D. et al. "Recent advances in nanopore sequencing," *Electrophoresis*, vol. 33, pp. 3418-3428, 2012.
Manrao, E. et al. "Reading DNA at single-nucleotide resolution with a mutant MspA nanopore and phi29 DNA polymerase," *Nat Biotechnol*, 30(4), 6 pages, Mar. 25, 2012.
Marras, S. "Interactive Fluorophore and Quencher Pairs for Labeling Fluorescent Nucleic Acid Hybridization Probes," *Mol Biotechnol*, vol. 38, 247-255, Mar. 2008.
Marras, S. "Selection of Fluorophore and Quencher Pairs for Fluorescent Nucleic Acid Hybridization Probes," *Methods in Molecular Biology*, vol. 335, 3-16, 2006.
McNally, et al. "Optical recognition of converted DNA nucleotides for single•molecule DNA sequencing using nanopore arrays," *Nano Letters*, vol. 10, No. 6; pp. 2237-2244, Jun. 9, 2010.
Meagher, R. J. et al. "Free-solution electrophoresis of DNA modified with drag-tags at both ends," *Electrophoresis*, vol. 27, pp. 1702-1712, 2006.
Meagher, R. J. et al. "Sequencing of DNA by Free-Solution Capillary Electrophoresis Using a Genetically Engineered Protein Polymer Drag-Tag," *Anal. Chem.*, vol. 80, pp. 2842-2848, Apr. 15, 2008.
Medintz, I.L. et al. "A fluorescence resonance energy transfer-derived structure of a quantum dot-protein bioconjugate nonassembly," *PNAS*, 101(26), pp. 9612-9617, Jun. 29, 2004.
Medintz, I.L. et al. "Quantum dot bioconjugates for imaging, labelling and sensing," *Nature Materials*, vol. 4, 435-446, Jun. 2005.
Meller, A. et al., "Rapid nanopore discrimination between single polynucleotide molecules," *The National Academy of Sciences*, 2000, 7 pages.
Meller, A. et al., "Voltage-Driven DNA Translocations through a Nanopore," *Phys. Rev. Lett.* 86(15), pp. 3435-3438, Apr. 2001.
Meller, et al., "Single Molecule Measurements of DNA Transport through a Nanopore," *Electrophoresis*, vol. 23, pp. 2583-2591, 2002.
Metzker, M. "Sequencing technologies—the next generation," *Nature Review Genetics*, vol. 11, pp. 31-46, Jan. 2010.
Meyers, R. "Molecular Biology and Biotechnology, A Comprehensive Desk Reference," VCH Publisher, Inc., New York, NY, 1995, pp. 317-319.
Mir, K., "Ultrasensitive RNA profiling: Counting single molecules on microarrays," *Genome Research*,16:1195-1197, Oct. 2006.
Moerner, W.E. et al. "Methods of single-molecule fluorescence spectroscopy and microscopy," *Review of Scientific Instruments*, 74(8), pp. 3597-3619, Aug. 2003.
Nakane, J. et al, "Evaluation of nanopores as candidates for electronic analyte dectection," *Electrophoresis*, vol. 23, pp. 2592-2601, 2002.
Nakane, J. et al, "Nanopore sensors for nucleic acid analysis," *J. Phys. Condens. Matter*, Matter 15, pp. R1365-R1393, 2003.
Ogura, Y. et al., "A Frameshift Mutation in NOD2 Associated with Susceptibility to Crohn's Disease," *Nature*, vol. 411, pp. 603-606, May 31, 2001, Macmillan Magazine Ltd.
Paul, N. et al. "PCR incorporation of modified dNTPs: the substrate properties of biotinylated dNTPs," *Biotechniques*, 48(4), 333-334, Apr. 2010.
PCT International Patent Application No. PCT/US2010/034809 filed May 13, 2010 in the name of Huber, International Search Report and Written Opinion dated Feb. 6, 2014.
PCT International Patent Application No. PCT/US2010/034809 filed May 13, 2010 in the name of Huber, International Search Report and Written Opinion dated Sep. 13, 2010.
PCT International Patent Application No. PCT/US2011/54365 filed Sep. 30, 2011 in the name of Huber et al., International Search Report and Written Opinion dated Apr. 25, 2012.

(56) References Cited

OTHER PUBLICATIONS

PCT International Patent Application No. PCT/US2013/067126 filed Oct. 28, 2013 in the name of Huber, International Search Report and Written Opinion dated May 6, 2014.
PCT International Patent Application No. PCT/US2014/039444 filed May 23, 2014 in the name of Huber et al., International Search Report and Written Opinion dated Dec. 3, 2014.
PCT International Patent Application No. PCT/US2015/054756 filed Oct. 8, 2015 in the name of Huber et al., International Search Report and Written Opinion dated Jan. 6, 2016.
PCT International Patent Application No. PCT/US2015/057245 filed Oct. 23, 2015 in the name of Huber et al., International Preliminary Report on Patentability dated Nov. 15, 2016.
PCT International Patent Application No. PCT/US2015/057245 filed Oct. 23, 2015 in the name of Huber et al., International Search Report and Written Opinion dated Jan. 21, 2016.
Ramachandran, G. et al. "Current bursts in lipid bilayers initiated by colloidal quantum dots," *Applied Physics Letter*, 86:083901-1 to 083901-3, Feb. 17, 2005.
Ramsay, N. et al. "CyDNA: Synthesis and Replication of Highly Cy-Dye Substituted DNA by an Evolved Polymerase," *J. Am. Chem. Soc.*, vol. 132, 5096-5104, Mar. 2010.
Randolph, JB et al. "Stability, specificity and fluorescence brightness of multiply-labeled fluorescent DNA probes," *Nucleic Acids Research*, 25(14) 2923-2929, May 1997.
Rasnik, I. et al., "Nonblinking and long-lasting single-molecule fluorescence imaging," *Nature Methods*, 3(11), pp. 891-893, Nov. 2006.
Reed, M.A. "Quantum Dots," *Scientific American*, pp. 118-123, Jan. 1993.
Resch-Genger, U. et al. "Quantum dots versus organic dyes as fluorescent labels," *Nature Methods*,5(9), pp. 763-775, Sep. 2008.
Rhee, M. et al., "Nanopore Sequencing Technology: Nanopore Preparations," *Trends in Biotechnology*, vol. 25, No. 4, pp. 174-181, Apr. 2007.
Rhee, M. et al., "Nanopore Sequencing Technology: research trends and applications," *Trends in Biotechnology*, vol. 24, No. 12, pp. 580-586, Dec. 2008.
Sabanayagam, C.R. et al., "Long time scale blinking kinetics of cyanine fluorophores conjugated to DNA and its effect on Forster resonance energy transfer," *J. Chem. Phys.*, 123(22), pp. 224708-1 to 224708-7, Dec. 2005.
Sanger, F. et al., "DNA Sequencing with Chain-Terminating Inhibitors," *Proc. Natl. Acad. Sci. USA*, vol. 74, No. 12, pp. 5463-5467, Dec. 1977.
Sauer, M. et al. "Single molecule DNA sequencing in submicrometer channels: state of the art and future prospects," *Journal of Biotechnology*, 86(3), 181-201, Apr. 2001.
Schumacher, S. et al, "Highly-integrated lab-on-chip system for point-of-care multiparameter analysis," *Lab on a Chip*, 12(3), pp. 464-473, 2012.
Seela, F. et al. "Fluorescent DNA: the development of 7-deazapurine nucleoside triphosphates applicable for sequencing at the single molecule level," *Journal of Biotechnology*, 86(3), 269-279, Apr. 2001.
Shaffer, C., "Next generation sequencing outpaces expectations," *Nature Biotechnology*, vol. 25, p. 149, Feb. 2007.
Shi, L. et al. "Luminescent Quantum Dots Fluorescence Resonance Energy Transfer-Based Probes for Enzymatic Activity and Enzyme Inhibitors," *Anal. Chem*, 79(1), pp. 208-214, Jan. 1, 2007.
Song, L. et al., "Structure of Staphylococcal alpha-hemolysin, a heptameric transmembrane protein," *Science*, vol. 274, No. 5294, pp. 1859-1866, Dec. 13, 1996.
Soni, et al. "Progress toward Ultrafast DNA Sequencing Using Solid-State Nanopores," *Clinical Chemistry*, vol. 53, No. 11; pp. 1996-2001, 2007.
Soni, G. V. et al. "Synchronous optical and electrical detection of biomolecules traversing through solid-state nanopores," *Review of Scientific Instruments*, pp. 014301-1-014301-7, published online Jan. 19, 2010.

Stephan, J. et al. "Towards a general procedure for sequencing single DNA molecules," *Journal of Biotechnology*, 86(3) 255-267, Apr. 2001.
Storm, A. J. et al. "Fabrication of solid-state nanopores with single-nanometre precision," *Nature Materials*, vol. 2, pp. 537-540, Aug. 2003.
Strittmatter, W.J. et al, "Apolipoprotein E and Alzheimer's Disease," *Annual Review of Neuroscience*, vol. 19, pp. 53-77, 1996.
Stryer, L. et al. "Diffusion-enhanced fluorescence energy transfer," *Annual review of biophysics and bioengineering*, vol. 11. No. 1; pp. 203-222, 1982.
Stryer, L., "Fluorescence Energy Transfer as a Spectroscopic Ruler," *Annual Review of Biochemistry*, vol. 47, pp. 819-846, Jul. 1978.
Tamura, T., *Molecular Biology Illustrated*,revised Second Edition, pp. 174-175, Jan. 1, 2003.
Tasara, T. et al. "Incorporation of reporter molecule-labeled nucleotides by DNA polymerases. II. High-density labeling of natural DNA," *Nucleic Acids Research*, 31(10), 2636-2646, May 2003.
Telenius, H. et al., "Degenerate oligonucleotide-primed PCR: General amplification of target DNA by a single degenerate primer," *Genomics*, vol. 13, No. 3, pp. 718-725, Jul. 1992.
Thompson, J. F. et al. "The properties and applications of single-molecule DNA sequencing," *Genome Biology*, 12(217), 10 pages, 2011.
Tucker, T. et al, "Massively Parallel Sequencing: The Next Big Thing in Genetice Medicine," *Am. J. Human Genet.*, vol. 85, pp. 142-154, Aug. 2009.
Turner, E. et al, "Methods for Genomic Partitioning," *Annual Review of Genomics and Human Genetics*, vol. 10, pp. 263-284, 2009.
U.S. Appl. No. 13/426,515, filed Mar. 21, 2012 in the name of Huber, Non-final Office Action dated Dec. 2, 2013.
U.S. Appl. No. 13/426,515, filed Mar. 21, 2012 in the name of Huber, Notice of Allowance dated Apr. 11, 2014.
U.S. Appl. No. 13/662,532, filed Oct. 28, 2012 in the name of Huber, Final Office Action dated Mar. 17, 2015.
U.S. Appl. No. 13/662,532, filed Oct. 28, 2012 in the name of Huber, Non-final Office Action dated Aug. 7, 2014.
U.S. Appl. No. 13/662,532, filed Oct. 28, 2012 in the name of Huber, Non-final Office Action dated Dec. 20, 2013.
U.S. Appl. No. 14/018,376, filed Sep. 4, 2013 in the name of Huber, Final Office Action dated Sep. 24, 2015.
U.S. Appl. No. 14/018,376, filed Sep. 4, 2013 in the name of Huber, Non-final Office Action dated Mar. 3, 2015.
U.S. Appl. No. 14/285,474, filed May 22, 2014 in the name of Huber, Non-final Office Action dated Apr. 30, 2015.
U.S. Appl. No. 14/285,474, filed May 22, 2014 in the name of Huber, Notice of Allowance dated Nov. 20, 2015.
U.S. Appl. No. 61/168,431, filed Apr. 10, 2009.
Venkatesen, B. M. et al. "Lipid bilayer coated Al2O3 naopore sensors: towards a hybrid biological solid-state nanopore," *Biomed Microdevices*, 13(4), 21 pages, 2011.
Venkatesen, B. M. et al. "Nanopore sensors for nucleic acid analysis," *Nature Nanotechnology*,vol. 6, pp. 615-624, Oct. 2011.
Vercoutere, W. et al., "Rapid discrimination among individual DNA hairpin molecules at single-nucleotide resolution using an ion channel," *Nature Biotechnology*, vol. 19, pp. 248-252, Mar. 2001.
Voelkerding, K. et al, "Next-Generation Sequencing: From Basic Research to Diagnostic," *Clinical Chemistry*, 55:4, pp. 641-658, 2009.
Walker, B. et al. "Key Residues for Membrane Binding, Oligomerization, and Pore Forming Activity of Staphylococcal alpha-Hemolysin Identified by Cysteine Scanning Mutagenesis and Targeted Chemical Modification," *Journal of Biological Chemistry*, 270(39), pp. 23065-23071, Sep. 29, 1995.
Wang, H. et al., "Nanopores with a spark for single-molecule detection," *Nature Biotechnology*, vol. 19, pp. 622-633, Jul. 2001.
Wanunu, M. et al. "Chemically Modified Solid-State Nanopores," *Nano Letters*, 7(6), pp. 1580-1585, 2007.

(56) References Cited

OTHER PUBLICATIONS

Wanunu, M. et al. "Nanopores: A journey towards DNA sequencing," *Physics of Life Reviews*, vol. 9, pp. 125-158, 2012.

White et al., "Single Ion-Channel Recordings Using Glass Nanopore Membranes," *J. Amer. Chem. Soc.*, 129:11766-11775, Sep. 5, 2007.

Won, J. et al. "Protein polymer drag-tags for DNA separations by end-labeled free electrophoresis," *Electrophoresis*, vol. 26, pp. 2138-2148, 2005.

Wu, X. et al, "Microfluidic differential resistive pulse sensors," *Electrophoresis*, 29(13), pp. 2754-2759, 2008.

Xu, et al., "Perspectives and Challenges of Emerging Single-Molecule DNA Sequencing Technologies," *SMALL*, 5(53), pp. 2638-2649, Dec. 4, 2009.

Yan, X. et al, "Parallel Fabrication of Sub-50-nm Uniformly Sized Nanaparticles by Deposition through a Patterned Silicon Nitride Nanostencil," *Nano Letters*, 5(6), pp. 1129-1134, 2005.

Yang, J. et al. "Rapid and precise scanning helium ion microscope milling of solid-state nanopores for biomolecule detection," *Nanotechnology*, vol. 22, 6 pages, 2011.

Yu, H. et al. "Cyanine dye dUTP analogs for enzymatic labeling of DNA probes," *Nucleic Acids Research*, 22(15), 3226-3232, Apr. 1994.

Yu, Y. et al. "Facile preparation of non-self-quenching fluorescent DNA strands with the degree of labeling up to the theoretic limit," *Chem. Commun.*, vol. 48, 6360-6362, May 2012.

Zhang, L. et al., "Whole genome amplification from a single cell: implications for genetic analysis," *Proc. Natl. Acad. Sci. USA*, vol. 89, No. 13, pp. 5847-5851, Jul. 1, 1992.

Zhe, J. et al, "A micromachined high throughput Coulter counter for bioparticle detection and counting," *J. Micromech. Microeng.*, vol. 17, pp. 304-313, 2007.

Zheng, S. et al. "Parallel analysis of biomolecules on a microfabricated capillary array chip," *Electrophoresis*, vol. 26, abstract only, Mar. 2006.

Zhu, Z. et al. "Directly labeled DNA probes using fluorescent nucleotides with different length linkers," *Nucleic Acids Research*, 22(16), 3418-3422, Aug. 1994.

Zwolak, M. et al., "Colloquium: Physical approaches to DNA sequencing and detection," *Reviews of Modern Physics*, 80(1), pp. 141-165, Jan. 2, 2008.

\* cited by examiner

SEQUENCE LISTING

```
<160> NUMBER OF SEQ ID NOS: 2

<210> SEQ ID NO 1
<211> LENGTH: 116
<212> TYPE: DNA
<213> ORGANISM: Artificial Sequence
<220> FEATURE:
<223> OTHER INFORMATION: polynucleotide

<400> SEQUENCE: 1
aacggccctt cgatctcatt gaggatgaga ggagagtcaa aggaagaacg aggatgagag      60
gagagtgaga gcaaaggaag aacgaggatg agaggagagt gagagcaaag gaagaa        116

<210> SEQ ID NO 2
<211> LENGTH: 90
<212> TYPE: DNA
<213> ORGANISM: Artificial Sequence
<220> FEATURE:
<223> OTHER INFORMATION: polynucleotide
```

-continued

```
<400> SEQUENCE: 2
gctatgtggc gcggtattat taagaaggag actgagagga gagaaggagc aagaaggaaa      60
tgagagcgag aggagagaag gaggaagaag                                       90
```

NANOPORE-BASED NUCLEIC ACID ANALYSIS WITH MIXED FRET DETECTION

CROSS-REFERENCE TO RELATED APPLICATIONS

This application is filed under 35 U.S.C. §371 claiming priority from International Application No. PCT/US14/39444, filed May 23, 2014, which claims benefit of priority to U.S. Provisional Pat. Appl. No. 61/827,519, filed May 24, 2013, all of which are incorporated by reference herein in their entireties.

BACKGROUND

DNA sequencing technologies developed over the last decade have revolutionized the biological sciences, e.g. Lerner et al, The Auk, 127: 4-15 (2010); Metzker, Nature Review Genetics, 11: 31-46 (2010); Holt et al, Genome Research, 18: 839-846 (2008); and have the potential to revolutionize many aspects of medical practice, e.g. Voelkerding et al, Clinical Chemistry, 55: 641-658 (2009); Anderson et al, Genes, 1: 38-69 (2010); Freeman et al, Genome Research, 19: 1817-1824 (2009); Tucker et al, Am. J. Human Genet., 85: 142-154 (2009). However, to realize such potential there are still a host of challenges that must be addressed, including reduction of per-run sequencing cost, simplification of sample preparation, reduction of run time, increasing read lengths, improving data analysis, and the like, e.g. Baker, Nature Methods, 7: 495-498 (2010); Kircher et al, Bioessays, 32: 524-536 (2010); Turner et al, Annual Review of Genomics and Human Genetics, 10: 263-284 (2009). Single molecule sequencing using nanopores may address some of these challenges, e.g., Maitra et al, Electrophoresis, 33: 3418-3428 (2012); Venkatesan et al. Nature Nanotechnology, 6: 615-624 (2011); however, this approach has its own set of technical difficulties, such as, reliable nanopore fabrication, control of DNA translocation rates, nucleotide discrimination, detection of electrical signals from large arrays of nanopore sensors, and the like, e.g. Branton et al, Nature Biotechnology, 26(10): 1146-1153 (2008); Venkatesan et al (cited above).

Optical detection of nucleotides has been proposed as a potential solution to some of the technical difficulties in the field of nanopore sequencing, e.g. Huber, International patent publication WO 2011/040996; Russell, U.S. Pat. No. 6,528,258; Pittaro, U.S. patent publication 2005/0095599; Joyce, U.S. patent publication 2006/0019259; Chan, U.S. Pat. No. 6,355,420; McNally et al, Nano Lett., 10(6): 2237-2244 (2010); and the like. However, optically-based nanopore sequencing has not been realized for a variety of reasons, including the lack of suitable fabrication techniques and understanding of how elements of such systems interact.

In view of the above, it would be advantageous to nanopore sensor technology in general and its particular applications, such as optically based nanopore sequencing, if there were available materials and configurations of optical elements that permitted successful optical sensing and analysis of analytes, such as sequences of nucleic acids.

SUMMARY

Various methods for optical detection and analysis of polymers, such as polynucleotides, in microfluidic and/or nanofluidic devices, such as those using nanopores for determining sequences of nucleic acids are provided herein.

In certain variations, a method of determining a nucleotide sequence of a polynucleotide comprises the following steps: (a) translocating a polynucleotide, e.g., a single or double stranded polynucleotide, through a nanopore so that nucleotides of the polynucleotide pass in sequence by a first member of a FRET pair positioned adjacent to the nanopore, a plurality of the nucleotides being within a FRET distance of the first member of the FRET pair as the nucleotides exit the nanopore and at least a portion of the nucleotides being labeled with a second member of the FRET pair; (b) exposing the FRET pairs adjacent to the nanopore to a light beam so that FRET occurs between the first and a plurality of second members of the FRET pair within the FRET distance to generate a mixed FRET signal; (c) measuring mixed FRET signals as the polynucleotide translocates through the nanopore; and (d) determining a nucleotide sequence of the polynucleotide from the mixed FRET signals. In some embodiments, the nanopore is disposed in a solid phase membrane and the first member of a FRET pair is attached to the solid phase membrane adjacent to said nanopore. In other embodiments, the nanopore is a protein nanopore and the first member of a FRET pair is attached to the protein nanopore.

In another variation, a method of determining a nucleotide sequence of a polynucleotide comprises the following steps: (a) translocating a polynucleotide, e.g., a single or double stranded polynucleotide, through a nanopore having an exit so that nucleotides of the polynucleotide pass in sequence through a FRET zone upon exiting the nanopore, the FRET zone encompassing a plurality of the nucleotides during such passage and at least a portion of the nucleotides being labeled with at least one second member of a FRET pair and at least one first member of the FRET pair being in the FRET zone; (b) exposing the first and second members of the FRET pair in the FRET zone to a light beam so that FRET occurs between first and second members of the FRET pair to generate a mixed FRET signal; (c) measuring mixed FRET signals as the polynucleotide moves through the FRET zone; and (d) determining a nucleotide sequence of the polynucleotide from the mixed FRET signals.

In another variation, a method of determining a nucleotide sequence of a polynucleotide comprises the following steps: (a) translocating a polynucleotide, e.g., a single or double stranded polynucleotide, with labeled nucleotides through a nanopore dimensioned so that labels on the nucleotides are constrained to suppress FRET reactions, the labels on the nucleotides being second members of a FRET pair, and so that nucleotides of the polynucleotide pass in sequence through a FRET zone upon exiting the nanopore, the FRET zone encompassing a plurality of the nucleotides during such passage and at least one first member of the FRET pair being in the FRET zone; (b) exposing the first and second members of the FRET pair in the FRET zone to a light beam so that FRET occurs between the first and second members to generate a mixed FRET signal; (c) measuring mixed FRET signals as the polynucleotide moves through the FRET zone; and (d) determining a nucleotide sequence of the polynucleotide from the mixed FRET signals.

Various methods, systems and devices are exemplified in a number of implementations and applications, some of which are summarized below and throughout the specification.

DETAILED DESCRIPTION

Figure 1A:
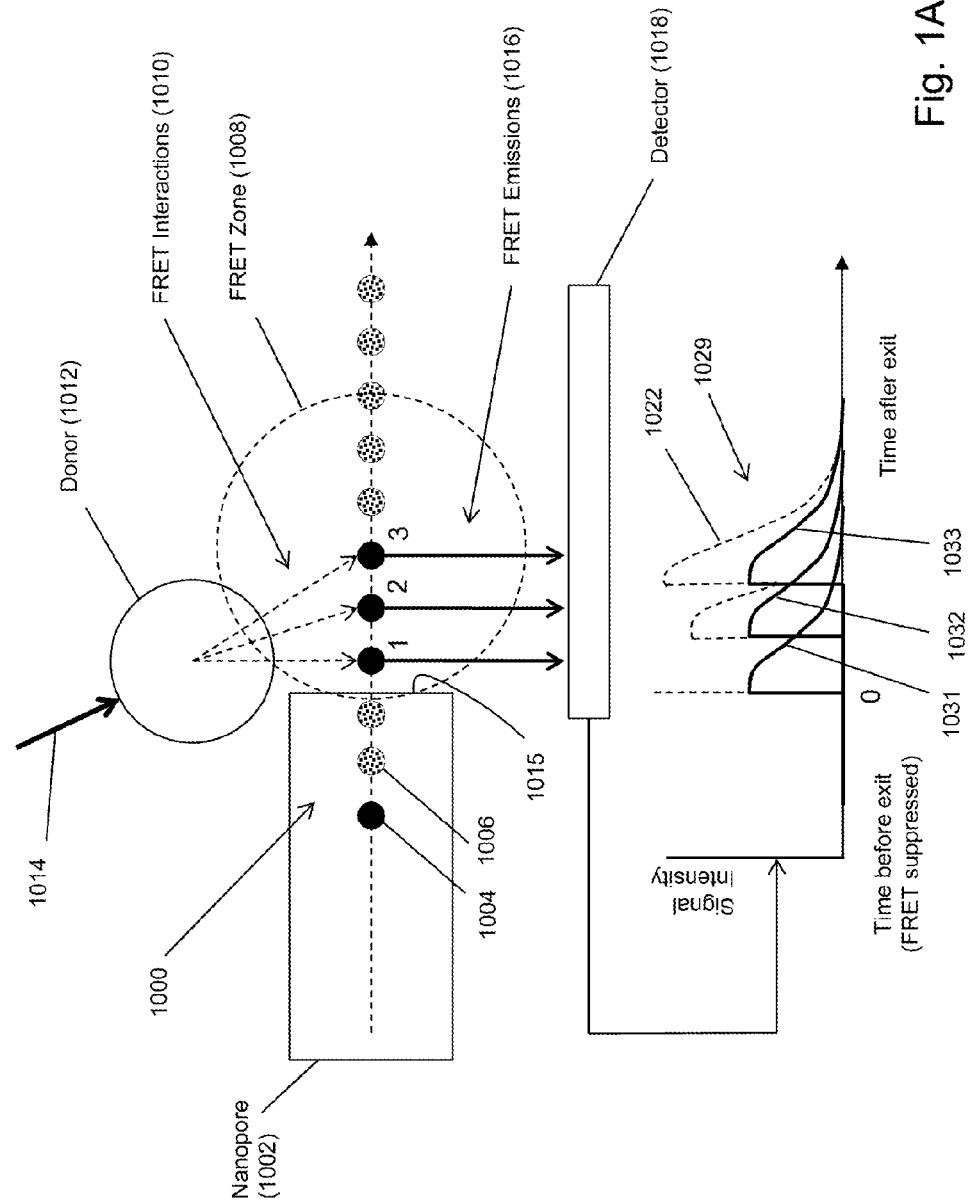
FIG. 1A illustrates schematically one embodiment with mixed FRET signal collection with a polynucleotide analyte labeled with a single kind of acceptor molecule.

While the various methods, systems and devices described herein are amenable to various modifications and alternative forms, specifics thereof have been shown by way of example in the drawings and will be described in detail. It should be understood, however, that the intention is not to be limited to the particular embodiments described. On the contrary, the intention is to cover all modifications, equivalents, and alternatives falling within the spirit and scope of the invention. For example, particular nanopore types and numbers, particular labels, FRET pairs, detection schemes, and fabrication approaches are shown for purposes of illustration. It should be appreciated, however, that the disclosure is not intended to be limiting in this respect, as other types of nanopores, arrays of nanopores, and other fabrication technologies may be utilized to implement various aspects of the systems discussed herein. Guidance for certain aspects is found in many available references and treatises well known to those with ordinary skill in the art, including, for example, Cao, Nanostructures & Nanomaterials (Imperial College Press, 2004); Levinson, Principles of Lithography, Second Edition (SPIE Press, 2005); Doering and Nishi, Editors, Handbook of Semiconductor Manufacturing Technology, Second Edition (CRC Press, 2007); Sawyer et al, Electrochemistry for Chemists, $2^{nd}$ edition (Wiley Interscience, 1995); Bard and Faulkner, Electrochemical Methods: Fundamentals and Applications, $2^{nd}$ edition (Wiley, 2000); Lakowicz, Principles of Fluorescence Spectroscopy, $3^{rd}$ edition (Springer, 2006); Hermanson, Bioconjugate Techniques, Second Edition (Academic Press, 2008); and the like, which relevant parts are hereby incorporated by reference.

Various methods and systems described herein relate to the use of nanopores and FRET pairs to measure properties of analytes, such as polymer analytes. A FRET pair generally is one or more FRET donors and one or more FRET acceptors where each donor is capable of a FRET reaction with each acceptor. In one aspect, this means that the donors of the FRET pair have an emission spectrum that substantially overlaps the absorption spectrum of the acceptors. In another aspect, the transition dipole of the donor and the acceptor have to be aligned in a way that allows efficient energy transfer. Certain variations in part are based on the recognition and appreciation of the use of FRET pairs under conditions where a plurality of FRET acceptors generate FRET signals during a detection event so that mixed FRET signals are collected. In some aspects, certain variations in part are also based on the discovery and appreciation of a FRET suppressing property of nanopores and the application of this property to enable detection of labeled analytes translocating through a nanopore. It is believed, although the variations described herein are not intended to be limited thereby, that a nanopore may be selected with a bore dimensioned so that a FRET pair label cannot orient to engage in a FRET interaction while translocating through the nanopore. The dipoles of the labels of the polynucleotide in the bore of the nanopore are constrained in their rotational freedom based on the limited diameter of the nanopore. This reduction in dipole alignment with the alignment of the corresponding FRET pair attached to the nanopore limits the FRET efficiency dramatically. Labeled polynucleotides can engage in a FRET interaction after exiting the nanopore at which point the FRET acceptor or donor on the analyte (e.g. polynucleotide) regains rotational freedom which allows for mixed FRET events.

A wide range of embodiments are contemplated depending on the type of analytes being detected, the types of donors and acceptors employed, the physical arrangement of the nanopore, donor and acceptors, whether analytes are labeled with donors or with acceptors, and the like. In one embodiment, analytes measured are acceptor-labeled polymers, especially acceptor-labeled polynucleotides. In one species of the latter embodiment, different nucleotides of a polynucleotide analyte are labeled with one or more different kinds of acceptors, so that a nucleotide sequence of the polynucleotide may be determined from measuring mixed FRET signals generated as it translocates through a nanopore. In another embodiment, analytes measured are donor-labeled polymers, especially donor-labeled polynucleotides. The sequence of the polynucleotide may be determined from measuring mixed FRET signals as it translocates through a nanopore. In yet another embodiment, at least one of the four nucleotides of a polynucleotide analyte is labeled with a member of a FRET pair. The positions of the labeled nucleotides in the polynucleotide are determined by translocating the labeled polynucleotide through a labeled nanopore and measuring FRET events. By labeling the remaining nucleotides of the same polynucleotide sample and subsequently translocating said samples through a labeled nanopore, sub-sequences of the polynucleotide are generated. Such sub-sequences can be re-aligned resulting in a full sequence of the polynucleotide.

Figure 1B:
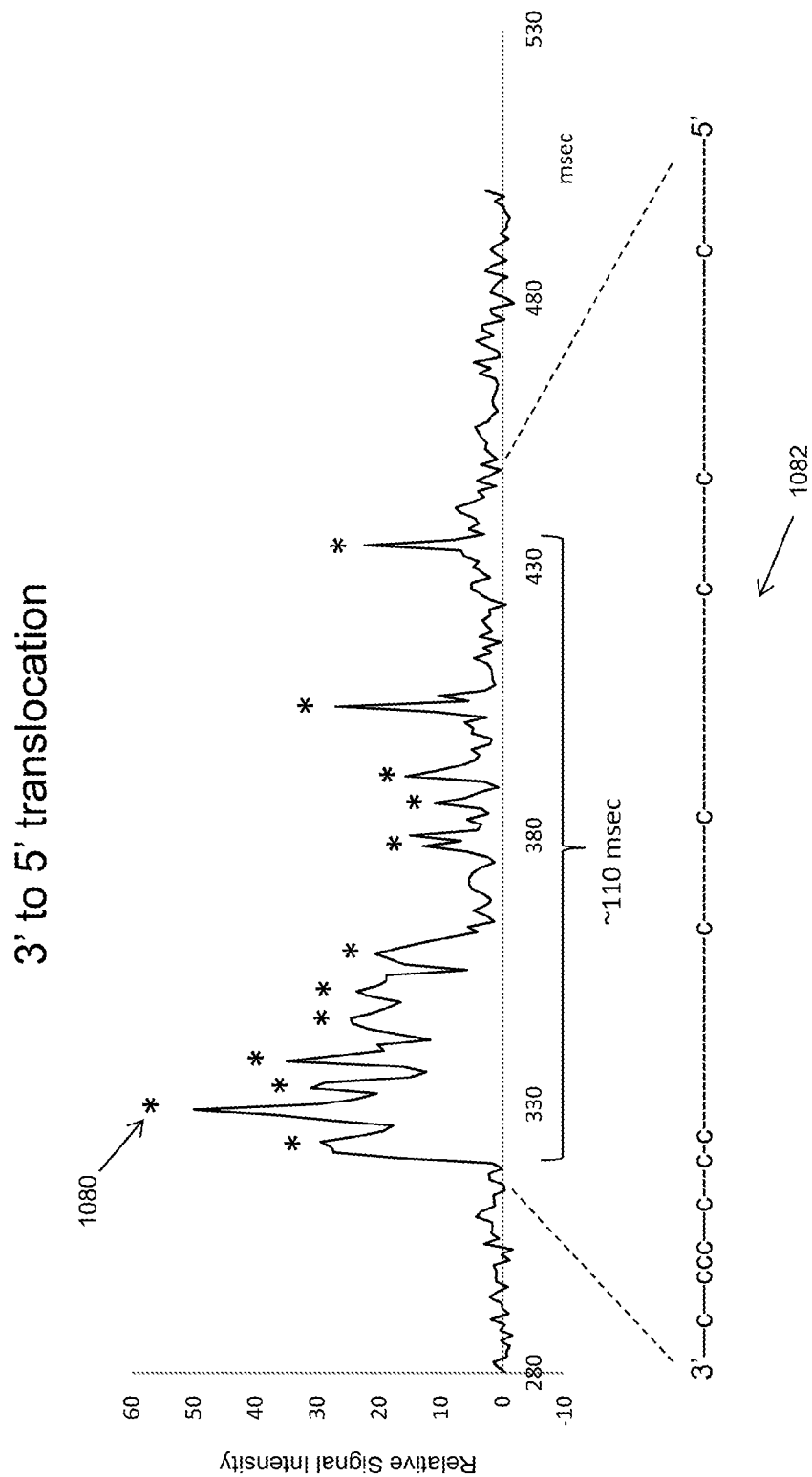
FIG. 1B shows data of mixed FRET signals of a test polynucleotide labeled with a single kind acceptor molecule.

Some of the above aspects and embodiments are illustrated diagrammatically in FIG. 1A. Polymer analyte (1000), such as a polynucleotide, is driven, e.g. electrophoretically, through nanopore (1002), which constrains the conformation of polymer (1000) so that its monomeric units translocate through the nanopore in the same order as their primary sequence in the polymer. Moreover, as mentioned above, whenever an acceptor-labeled monomeric unit is within the bore of nanopore (1002), FRET interactions between such acceptors and the donors of its FRET pair (e.g. 1012) are suppressed. Such suppression typically means that no detectable FRET signal is produced even if such acceptors are within a FRET distance of a donor due to unfavorable orientation of the acceptor and donor dipoles. On the other hand, as soon as an acceptor-labeled monomeric unit emerges from the bore of the nanopore into FRET zone (1008), a strong FRET signal is immediately produced (due to the proximity of donor (1012)), after which the signal decreases rapidly as the distance between the acceptor and donor increases, because translocation of polymer (1000) carries acceptors out of FRET zone (1008). FRET zone (1008), which is a spatial region immediately adjacent to exit (1015) of nanopore (1002), is defined by the FRET distances between donor (1012) and the acceptor labels attached to polymer (1000) as it translocates through and away from nanopore (1002). In FIG. 1A, only one type of monomeric unit, illustrated as solid circles (1004) is labeled; the rest of the monomeric units, illustrated as speckled circles (1006), are unlabeled. As illustrated, three labeled monomeric units (denoted "1", "2" and "3") are in FRET zone (1008). When donor (1012) is excited by excitation beam (1014), FRET interactions (1010) are generated and the three acceptors on the monomeric units produce FRET emissions (1016) that are collected by detector (1018) and recorded as mixed FRET signal intensity (1029). Signal intensity contributions from acceptors on monomeric units 1, 2 and 3 are illustrated by curves (1031, 1032 and 1033, respectively), which are combined by detector (1018) to give a mixed FRET signal shown by dashed curve (1022). In the example described below, an embodiment corresponding to that of FIG. 1A produced data shown in FIG. 1B for sequence (1082) 3'-AACGGCCCTTCGATCTCATrGAG-GATGAGAGGAGAGTCAAAGGAAGA-ACGAGGAT-GAGAGGAGAGTGAGAGCAAAGGAAGAACGAG-GATGAGAGG-AGAGTGAGAGCAAAGGAAGAA-5' (SEQ ID NO: 1), in which only cytosines are labeled. In FIG. 1B, only the relative positions of the labeled C's are shown so that the correspondence between such positions and peaks in the data can be appreciated. Intensity peaks are indicated by asterisks, such as that of (1080). The data is a plot of relative mixed FRET signal intensity versus time for the translocation in a 3'-first orientation of sequence (1082).

Figure 1C:
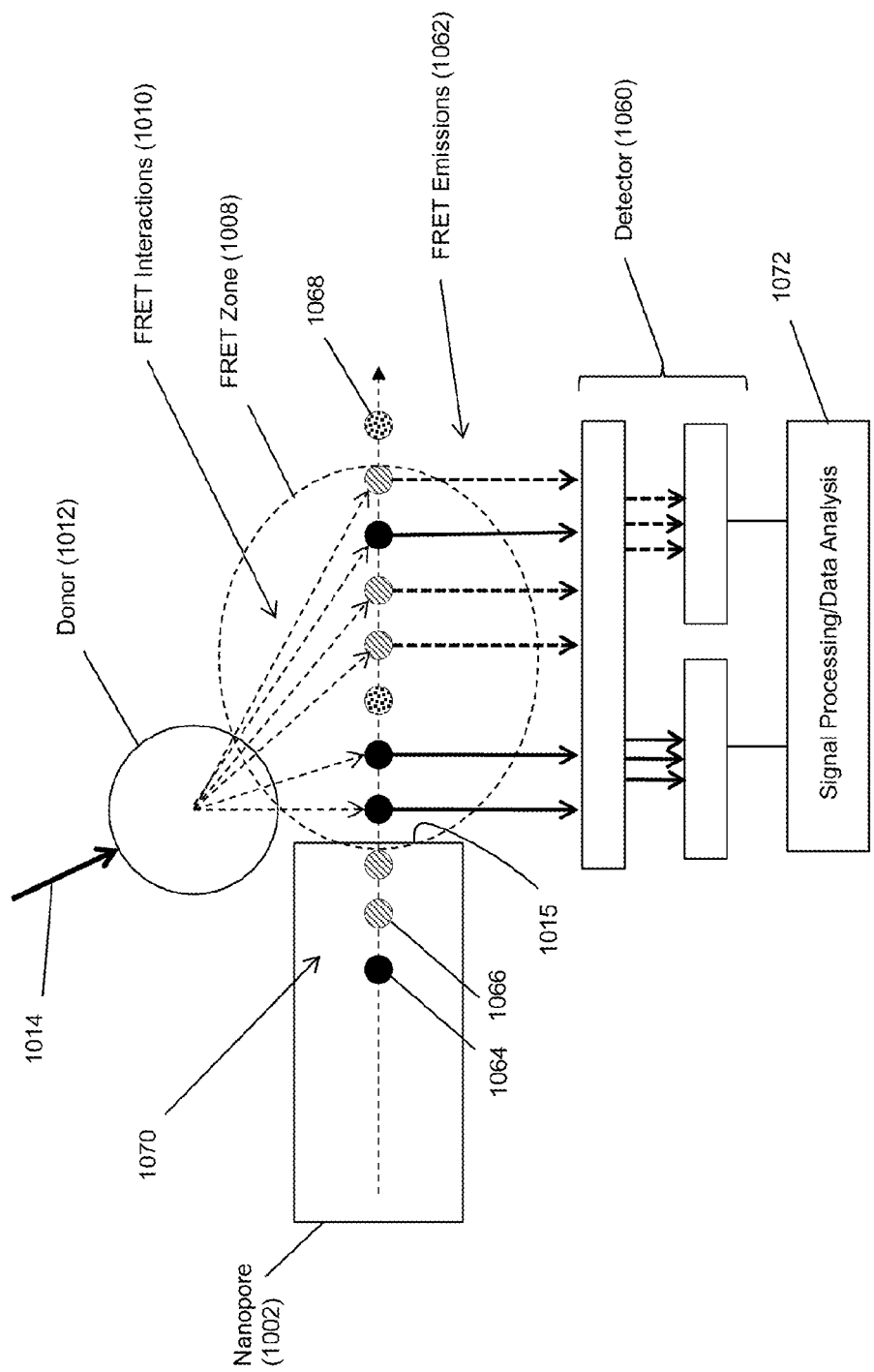
FIG. 1C illustrates schematically another embodiment with mixed FRET signal collection with a polynucleotide analyte labeled with two kinds of acceptor molecules.

Embodiments are provided where different acceptor labels are attached to different kinds of monomeric units, so that signals having different characteristics, e.g. frequency, intensity, wavelength, etc., are generated for different kinds of monomeric units, thereby permitting the different kinds of monomeric units to be distinguished. In one such embodiment, at least two different acceptor labels are used to label different nucleotides of a target polynucleotide. An apparatus for such an embodiment is illustrated in FIG. 1C. Polynucleotide (1070) comprises cytosines (or cytidines or deoxycytidines) labeled with a first acceptor (solid circles, 1064), Thymidines or thymines labeled with a second acceptor (cross-hatched circles, 1066), and Guanines and Adenines unlabeled (speckled circles, 1068). As above, as polynucleotide (1070) translocates through nanopore (1002), nucleotides exit into FRET zone (1008) where acceptors (if present) become capable of engaging in a FRET reaction and generating FRET emissions (1062). Such emissions are collected by detector (1060) which has conventional optical components for separating FRET emissions (1062) in accordance with the different signal characteristics of the different acceptor labels being employed, such as wavelength which can be separated, for example, by a dichroic mirror and/or filters. As a result, an initially collected mixed FRET signal is split into two or more signals representing mixed FRET signals from different acceptors, which may be further processed by conventional components (1072). Also described more fully in the example below, an embodiment corresponding to that of FIG. 1C produced data shown in FIG. 1D for sequence (1092) 5' GCTATGTGGCGCGGTATTATTAAGAAGGA-GACTGAGAGGAGAGAAGGAGCAAGAAGGA AAT-GAGAGCGAGAGGAGAAGAAGGAGGAAGAAG 3' (SEQ ID NO: 2), in which only cytosines (or cytidines or deoxycytidines) and thymidines or thymines are labeled. Signals from first acceptors attached to T's are indicated by dashed line (1095) and signals from first acceptors attached to C's are indicated by solid line (1096) In FIG. 1D, the positions of the labeled T's and C's are shown as bolded letters (1051, 1052, 1053, 1054, 1055 and 1056, respectively). Intensity peaks in the plots corresponding to the labeled T's and C's are indicated by the same reference numbers. The data is a plot of relative mixed FRET signal intensity versus time for the translocation in a 3'-first orientation of sequence (1070).

As mentioned above, in one aspect, a method may be carried out by the following steps: (a) translocating a polynucleotide, e.g., a single stranded or double stranded polynucleotide, through a nanopore so that nucleotides of the polynucleotide pass in sequence by a first member of a FRET pair positioned adjacent to the nanopore, a plurality of the nucleotides being within a FRET distance of the first member of the FRET pair as the nucleotides exit the nanopore and a portion of the nucleotides being labeled with a second member of the FRET pair; (b) exposing the FRET pairs adjacent to the nanopore to a light beam so that FRET occurs between the first and a plurality of second members of the FRET pair within the FRET distance to generate a mixed FRET signal; (c) measuring mixed FRET signals as the polynucleotide translocates through the nanopore; and (d) determining a nucleotide sequence of the polynucleotide from the mixed FRET signals. In some embodiments, a nanopore is a hybrid nanopore comprising a protein nanopore inserted into a pore of a solid phase membrane, as described more fully below. In hybrid nanopores, a first member of a FRET pair may be attached directly to the protein nanopore, or alternatively, directly to the solid phase membrane using conventional linking chemistries, such as "click" chemistries, e.g. Kolb et al, Angew. Chem. Int. Ed., 4): 2004-2021 (2001), or the like. In one embodiment, a first member of a FRET pair is attached directly or indirectly to the protein nanopore, for example, as discussed in reference to FIG. 2D. In another embodiment, the first member of the FRET pair is a donor, such as a quantum dot. Quantum dots are typically much larger than acceptors, especially acceptors that are organic dyes, which typically have molecular weights in the range of from 200 to 2000 daltons. Thus, for FRET to occur between a quantum dot donor and a multiply-labeled polymer analyte, multiple acceptors are brought within a FRET distance of the quantum dot at the same time. Under such circumstances multiple FRET signals are generated within the same time interval over which such signals are collected, thereby giving rise to a mixed FRET signal.

Nanopores and Nanopore Sequencing

Nanopores used with various methods, systems and devices described herein may be solid-state nanopores, protein nanopores, or hybrid nanopores comprising protein nanopores configured in a solid-state membrane, or like framework. Important features of nanopores include (i) constraining analytes, particularly polymer analytes, to pass through a detection zone in sequence, (ii) compatibility with a translocating means, that is, whatever method is used to drive an analyte through a nanopore, and (iii) FRET suppression for members of FRET pairs within the lumen, or bore, of the nanopore.

Nanopores may be fabricated in a variety of materials including but not limited to, silicon nitride ($Si_3N_4$), silicon dioxide ($SiO_2$), and the like. The fabrication and operation of nanopores for analytical applications, such as DNA sequencing, are disclosed in the following exemplary references that are incorporated by reference: Russell, U.S. Pat. No. 6,528,258; Feier, U.S. Pat. No. 4,161,690; Ling, U.S.

Pat. No. 7,678,562; Hu et al, U.S. Pat. No. 7,397,232; Golovchenko et al, U.S. Pat. No. 6,464,842; Chu et al, U.S. Pat. No. 5,798,042; Sauer et al, U.S. Pat. No. 7,001,792; Su et al, U.S. Pat. No. 7,744,816; Church et al, U.S. Pat. No. 5,795,782; Bayley et al, U.S. Pat. No. 6,426,231; Akeson et al, U.S. Pat. No. 7,189,503: Bayley et al, U.S. Pat. No. 6,916,665; Akeson et al, U.S. Pat. No. 6,267,872; Meller et al, U.S. patent publication 2009/0029477; Howorka et al, International patent publication WO2009/007743; Brown et al, International patent publication WO2011/067559; Meller et al, International patent publication WO2009/020682; Polonsky et al, International patent publication WO2008/092760; Van der Zaag et al, International patent publication WO2010/007537; Yan et al, Nano Letters, 5(6): 1129-1134 (2005); Iqbal et al, Nature Nanotechnology, 2: 243-248 (2007); Wanunu et al, Nano Letters, 7(6): 1580-1585 (2007); Dekker, Nature Nanotechnology, 2: 209-215 (2007); Storm et al, Nature Materials, 2: 537-540 (2003); Wu et al, Electrophoresis, 29(13): 2754-2759 (2008); Nakane et al, Electrophoresis, 23: 2592-2601 (2002); Zhe et al, J. Micromech. Microeng., 17: 304-313 (2007); Henriquez et al, The Analyst, 129: 478-482 (2004): Jagtiani et al, J. Micromech. Microeng., 16: 1530-1539 (2006); Nakane et al, J. Phys. Condens. Matter, 15 R1365-R1393 (2003); DeBlois et al, Rev. Sci. Instruments, 41(7): 909-916 (1970); Clarke et al, Nature Nanotechnology, 4(4): 265-270 (2009); Bayley et al, U.S. patent publication 2003/0215881; and the like. Briefly, in one aspect, a 1-50 nm channel is formed through a substrate, usually a membrane, through which an analyte, such as DNA, is induced to translocate. The solid-state approach of generating nanopores offers robustness and durability as well as the ability to tune the size and shape of the nanopore, the ability to fabricate high-density arrays of nanopores on a wafer scale, superior mechanical, chemical and thermal characteristics compared with lipid-based systems, and the possibility of integrating with electronic or optical readout techniques. Biological nanopores on the other hand provide reproducible narrow bores, or lumens, especially in the 1-10 nanometer range, as well as techniques for tailoring the physical and/or chemical properties of the nanopore and for directly or indirectly attaching groups or elements, such as FRET donors or acceptors, by conventional protein engineering methods. Protein nanopores typically rely on delicate lipid bilayers for mechanical support, and the fabrication of solid-state nanopores with precise dimensions remains challenging. Combining solid-state nanopores with a biological nanopore overcomes some of these shortcomings, especially the precision of a biological pore protein with the stability of a solid state nanopore. For optical read out techniques a hybrid nanopore provides a precise location of the nanopore which simplifies the data acquisition greatly. The lateral diffusion of nanopore proteins inserted in a lipid bilayer makes an optical detection challenging. Since the biological part of a hybrid nanopore does not rely on the insertion in a lipid bilayer the degrees of freedom for modifications made to such a protein are greatly increased, e.g. a genetically modified nanopore protein that does not spontaneously insert in a lipid bilayer may still be used as a protein component of a hybrid nanopore. Bilayer destabilizing agents such as quantum dots may be used to label a protein component of a hybrid nanopore.

In one embodiment, a device or system for detecting one or more analytes, such as a polynucleotide analyte, comprises the following elements; (a) a solid phase membrane separating a first chamber and a second chamber, the solid phase membrane having at least one aperture connecting the first chamber and the second chamber through a bore; and (b) a first member of a fluorescent resonance energy transfer (FRET) pair attached to the at least one aperture, so that whenever one or more analytes having a plurality of second members of the FRET pair attached thereto traverses the bore, the plurality of second members are constrained to pass in sequence within a FRET distance of the first member of the FRET pair. In some embodiments, the solid phase membrane has been treated with a low energy ion beam to bleach its autofluorescence.

In another embodiment, a device or system for detecting a plurality of analytes, or a polymer analyte having a plurality of linked monomer units, such as nucleotides, is provided. Such an embodiment for determining a sequence of a polynucleotide may comprise one or more of the following elements: (a) a solid phase membrane separating a first chamber and a second chamber, the solid phase membrane having at least one aperture connecting the first chamber and the second chamber, and having a hydrophobic coating on at least one surface; (b) a lipid layer may be disposed on the hydrophobic coating; (c) a protein nanopore immobilized in the aperture, the protein nanopore having a bore with an exit, and the protein nanopore interacting with the lipid layer to form a seal with the solid phase membrane in the aperture so that fluid communication between the first chamber and the second chamber occurs solely through the bore of the protein nanopore, and the protein nanopore being dimensioned so that nucleotides of the polynucleotide pass through the exit of the bore in sequence and so that whenever nucleotides of the polynucleotide are labeled with second members of a FRET pair, FRET is suppressed between such second members inside the bore and first members of the FRET pair outside the bore; and/or (d) a first member of the FRET pair attached to the solid phase membrane or the protein nanopore, so that whenever nucleotides of the polynucleotide emerge from the bore, a plurality of the nucleotides are within a FRET distance of the first member of the FRET pair.

In some embodiments, the hydrophobic coating is optional in that the surface of the solid phase membrane is sufficiently hydrophobic itself so that a lipid layer adheres to it stably. The at least one aperture will have an inner surface, or wall, connected to, or contiguous with the surfaces of the solid phase membrane. In some embodiments, the at least one aperture will be a plurality of apertures, and the plurality of apertures may be arranged as a regular array, such as a rectilinear array of apertures, the spacing of which depending in part on the number and kind of FRET pairs employed and the optical detection system used. Each of the apertures has a diameter, which in some embodiments is such that a protein nanopore is substantially immobilized therein. In some embodiments, substantially immobilized means that a protein nanopore may move no more than 5 nm in the plane of the solid phase membrane relative to the wall of the aperture. In another embodiment, substantially immobilized means that a protein nanopore may move no more than 5 nm in the plane of the solid phase membrane relative to the wall of the aperture. The protein nanopores each have a bore, or passage, or lumen, which permits fluid communication between the first and second chambers when the protein nanopore is immobilized in an aperture. Generally, the bore is coaxially aligned with the aperture. One function of the hydrophobic layer is to provide a surface to retain lipids in and/or immediately adjacent to the at least one aperture. Such lipids, in turn, permit disposition and immobilization of a protein nanopore within an aperture in a functional conformation and in a manner that forms a fluid seal with the wall of the aperture. In some embodiments, such seal also prevents electrical current passing between the first and second chambers around the protein nanopore. In some embodiments, charged analytes are disposed in an electrolyte solution in the first chamber and are translocated through the bore(s) of the protein nanopore(s) into an electrolytic solution in the second chamber by establishing an electrical field across the solid phase membrane. For convenience of manufacture, in some embodiments the hydrophobic coating will be on one surface of the solid phase membrane and the wall(s) of the aperture(s).

In some embodiments, the solid phase membrane is treated with a low energy ion beam to bleach its autofluorescence, as described more fully below.

Figure 2A:
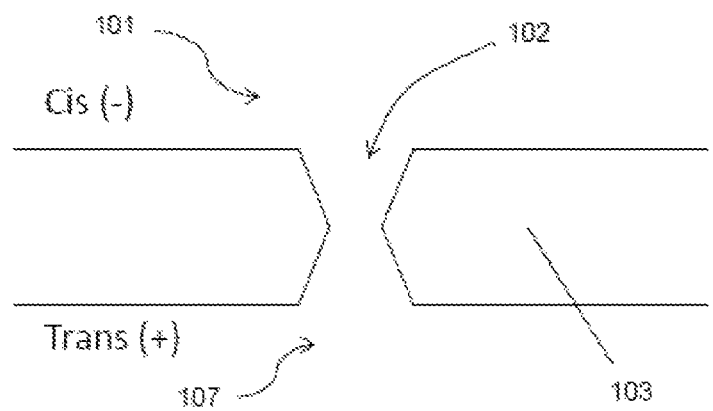
FIGS. 2A-2C illustrate one embodiment of a hybrid biosensor.
Figure 2B:
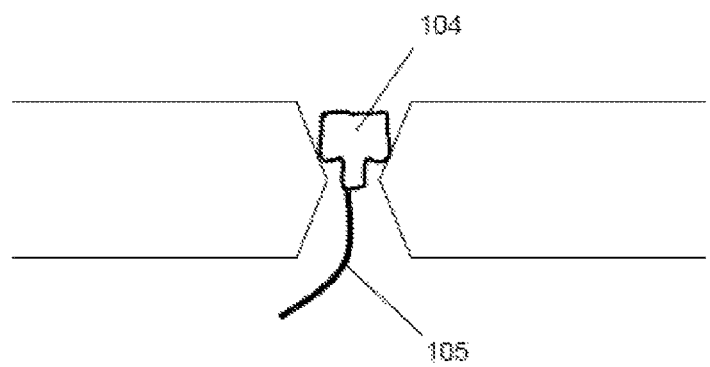
Figure 2C:
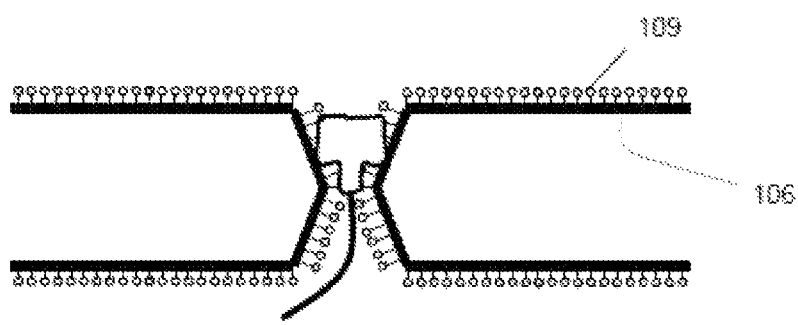

FIGS. 2A-2C are diagrams of hybrid biosensors. A nanometer sized hole (102) is drilled into a solid-state substrate, or solid phase membrane, (103) which separates two chambers, or compartments cis (101) and trans (107). A protein biosensor (e.g a protein nanopore) (104) attached to a charged polymer (105), such as a single or double-stranded DNA, is embedded into the solid-state nanohole by electrophoretic transport. In FIG. 1C the protein biosensor is inserted. In a nanometer sized hole which surface has a hydrophobic coating (106) and may have a lipid layer (109) attached thereto. A nanopore may have two sides, or orifices. One side is referred to as the "cis" side and faces the (−) negative electrode or a negatively charged buffer/ion compartment or solution. The other side is referred to as the "trans" side and faces the (+) electrode or a positively charged buffer/ion compartment or solution. A biological polymer, such as a labeled nucleic acid molecule or polymer can be pulled or driven through the pore by an electric field applied through the nanopore, e.g., entering on the cis side of the nanopore and exiting on the trans side of the nanopore.

Figure 2D:
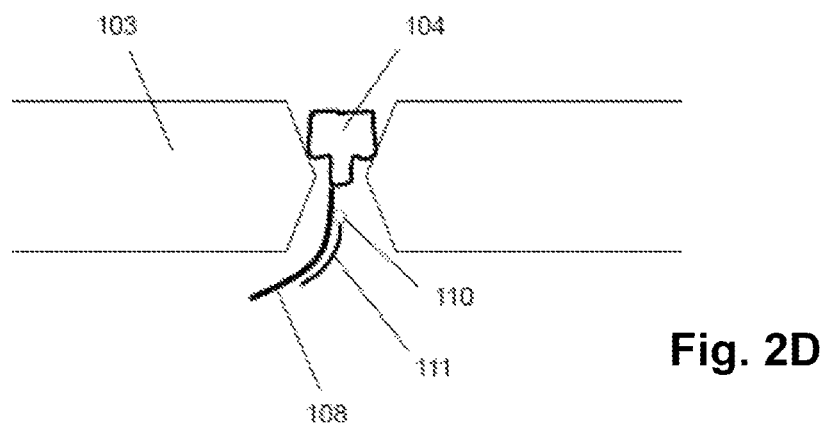
FIG. 2D illustrates an embodiment of a device with positioning of a member of a FRET pair using oligonucleotide hybridization.
Figure 2E:
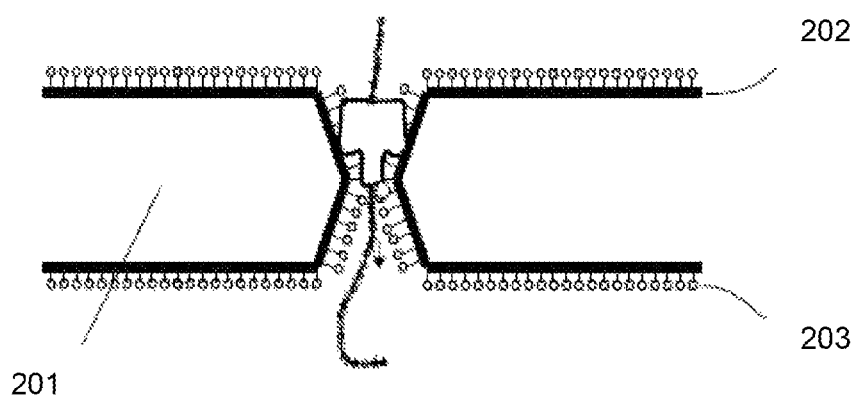
FIG. 2E illustrates one embodiment of a hybrid nanopore where the surface of the solid state membrane (201) is coated with a hydrophobic layer (202) to which a lipid layer is adhered (203). The lipids form a gigaohm seal with the inserted pore protein.

FIG. 2D shows protein nanopore (104) inserted into an aperture drilled in a solid state membrane (103). Attached to the protein nanopore (104) is an oligonucleotide (108) to which a complementary secondary oligonucleotide (111) is hybridized. Said secondary oligonucleotide (111) has one or more first or second members of a FRET pair (110) attached to it. Alternatively, a member of a FRET pair may be directly attached to an amino acid of a protein nanopore. For example, a hemolysin subunit may be modified by conventional genetic engineering techniques to substitute a cysteine for a suitably located amino acid adjacent to the exit of the nanopore, e.g. the threonine 129. An oligonucleotide or members of a FRET pair may be attached via the thio group of the cysteine using conventional linker chemistries, e.g. Hermanson (cited above).

In some embodiments, a hybrid nanopore is utilized, particularly for optical-based nanopore sequencing of polynucleotides. Such embodiments comprise a solid-state orifice, or aperture, into which a protein biosensor, such as a protein nanopore, is stably inserted. A protein nanopore (e.g. alpha hemolysin) may be attached to a charged polymer (e.g. double stranded DNA) which serves as a drag force in an applied electric field, and which may be used to guide a protein nanopore into an aperture in a solid-state membrane. In some embodiments, the aperture in the solid-state substrate is selected to be slightly smaller than the protein, thereby preventing it from translocating through the aperture. Instead, the protein will be embedded into the solid-state orifice. The solid-state substrate can be modified to generate active sites on the surface that allow the covalent attachment of the plugged-in protein biosensor resulting in a stable hybrid biosensor.

The polymer attachment site in the biosensor can be generated by protein engineering e.g. a mutant protein can be constructed that will allow the specific binding of the polymer. As an example, a cysteine residue may be inserted at the desired position of the protein. The cysteine can either replace a natural occurring amino acid or can be incorporated as an addition amino acid. Care must be taken not to disrupt the biological function of the protein. The terminal primary amine group of a polymer (i.e. DNA) is then activated using a hetero-bifunctional crosslinker (e.g. SMCC). Subsequently, the activated polymer is covalently attached to the cysteine residue of the protein biosensor. In some embodiments, the attachment of the polymer to the biosensor is reversible. By implementing a cleavable crosslinker, an easily breakable chemical bond (e.g. an S—S bond) is introduced and the charged polymer may be removed after insertion of the biosensor into the solid-state aperture.

For someone skilled in the art it is obvious that a wide variety of different approaches for covalent or non-covalent attachment methods of a charged polymer to the protein biosensor are possible and the above described approach merely serves as an example. The skilled artisan will also realize that a variety of different polymers may be used as a drag force, including, but not limited to, single or double stranded DNA, polyethyleneglycol (PEG), polyvinylpyrrolidone (PVP), poly-L-lysine, linear polysaccharides etc. It is also obvious that these polymers may exhibit either a negative (−) or positive (+) charge at a given pH and that the polarity of the electric field may be adjusted accordingly to pull the polymer-biosensor complex into a solid-state aperture.

In some embodiments, a donor fluorophore is attached to the protein nanopore. This complex is then inserted into a solid-state aperture or nanohole (3-10 nm in diameter) by applying an electric field across the solid state nanohole until the protein nanopore is transported into the solid-state nanohole to form a hybrid nanopore. The formation of the hybrid nanopore can be verified by (a) the inserting protein nanopore causing a drop in current based on a partial blockage of the solid-state nanohole and by (b) the optical detection of the donor fluorophore.

Once stable hybrid nanopores have formed single stranded, fluorescently labeled (or acceptor labeled) DNA may be added to the cis chamber (the chamber with the (+) electrode). The applied electric field forces the negatively charged ssDNA to translocate through the hybrid nanopore during which the labeled nucleotides get in close vicinity of the donor fluorophore. In certain variations, double stranded DNA may be utilized.

Solid state, or synthetic, nanopores may be prepared in a variety of ways, as exemplified in the references cited above. In some embodiments a helium ion microscope may be used to drill the synthetic nanopores in a variety of materials, e.g. as disclosed by Yang et al, Nanotechnolgy, 22: 285310 (2011), which is incorporated herein by reference. A chip that supports one or more regions of a thin-film material, e.g. silicon nitride, that has been processed to be a free-standing membrane is introduced to the helium ion microscope (HIM) chamber. HIM motor controls are used to bring a free-standing membrane into the path of the ion beam while the microscope is set for low magnification. Beam parameters including focus and stigmation are adjusted at a region adjacent to the free-standing membrane, but on the solid substrate. Once the parameters have been properly fixed, the chip position is moved such that the free-standing membrane region is centered on the ion beam scan region and the beam is blanked. The HIM field of view is set to a dimension (in μm) that is sufficient to contain the entire anticipated nanopore pattern and sufficient to be useful in future optical readout (i.e. dependent on optical magnification, camera resolution, etc.). The ion beam is then rastered once through the entire field of view at a pixel dwell time that results in a total ion dose sufficient to remove all or most of the membrane autofluorescence. The field of view is then set to the proper value (smaller than that used above) to perform lithographically-defined milling of either a single nanopore or an array of nanopores. The pixel dwell time of the pattern is set to result in nanopores of one or more predetermined diameters, determined through the use of a calibration sample prior to sample processing. This entire process is repeated for each desired region on a single chip and/or for each chip introduced into the HIM chamber.

In some embodiments, the solid-state substrate may be modified to generate active sites on the surface that allow the covalent attachment of the plugged in protein biosensor or to modify the surface properties in a way to make it more suitable for a given application. Such modifications may be of covalent or non-covalent nature. A covalent surface modification includes a silanization step where an organosilane compound binds to silanol groups on the solid surface. For instance, the alkoxy groups of an alkoxysilane are hydrolyzed to form silanol-containing species. Reaction of these silanes involves four steps. Initially, hydrolysis of the labile groups occurs. Condensation to oligomers follows. The oligomers then hydrogen bond with hydroxyl groups of the substrate. Finally, during drying or curing, a covalent linkage is formed with the substrate with concomitant loss of water. For covalent attachment organosilanes with active side groups may be employed. Such side groups consist of, but are not limited to epoxy side chain, aldehydes, isocyanates, isothiocyanates, azides or alkynes (click chemistry) to name a few. For someone skilled in the art it is obvious that multiple ways of covalently attaching a protein to a surface are possible. For instance, certain side groups on an organosilane may need to be activated before being capable of binding a protein (e.g. primary amines or carboxyl side groups activated with an N-hydroxysuccinimidester). Another way of attaching a protein to the solid surface may be achieved through affinity binding by having one affinity partner attached to the protein and the second affinity partner being located on the solid surface. Such affinity pairs consist of the group of, but are not limited to biotin-strepavidin, antigen-antibody and aptamers and the corresponding target molecules.

In one embodiment, the surface modification of the solid state nanopore includes treatment with an organosilane that renders the surface hydrophobic. Such organosilanes include but are not limited to, alkanesilanes (e.g. octadecyldimethylchlorosilane) or modified alkanesilanes such as fluorinated alkanesilanes with an alkane chain length of 5 to 30 carbons. The hydrophobic surface may then be treated with a dilute solution of a lipid in pentane. After drying of the solvent and immersing the surface in an aqueous solution the lipid will spontaneously form a layer on the surface. A layer of lipid on the solid surface might prove beneficial for the formation of a hybrid nanopore. The lipid layer on the solid phase might reduce the leak current between protein and solid state nanopore and it might increase the stability of the inserted protein pore. Combining a low capacitance solid substrate as well as a lipid coating of said substrate may render the hybrid nanopore system amenable to an electrical readout based on current fluctuations generated by translocation of DNA through the hybrid nanopore. To achieve electrical read out with such a system a means of decreasing the translocation speed of unmodified DNA must be combined with a lipid coated hybrid nanopore. Molecular motors such as polymerases or helicases may be combined with a hybrid nanopore and effectively reduce the translocation speed of DNA through the hybrid nanopore. The lipids used for coating the surface may be from the group of sphingolipids, phospholipids or sterols.

A method and/or system for sequencing a biological polymer or molecule (e.g., a nucleic acid) may include exciting one or more donor labels attached to a pore or nanopore. A biological polymer may be translocated through the pore or nanopore, where a monomer of the biological polymer is labeled with one or more acceptor labels. Energy may be transferred from the excited donor label to the acceptor label of the monomer as, after the labeled monomer passes through, exits or enters the pore or nanopore. Energy emitted by the acceptor label as a result of the energy transfer may be detected, where the energy emitted by the acceptor label may correspond to or be associated with a single or particular monomer (e.g., a nucleotide) of a biological polymer. The sequence of the biological polymer may then be deduced or sequenced based on the detection of the emitted energy from the monomer acceptor label which allows for the identification of the labeled monomer. A pore, nanopore, channel or passage, e.g., an ion permeable pore, nanopore, channel or passage may be utilized in the systems and methods described herein.

The nanopore may have one or more labels attached. In some embodiments, the label is a member of a Forster Resonance Energy Transfer (FRET) pair. Such labels may comprise organic fluorophores, chemiluminescent labels, quantum dots, metallic nanoparticles and fluorescent proteins. The nucleic acid may have one distinct label per nucleotide. The labels attached to the nucleotides consist of the group of organic fluorophores, chemiluminescent labels, quantum dots, metallic nanoparticles and fluorescent proteins. The label attachment site in the pore protein can be generated by protein engineering e.g. a mutant protein can be constructed that will allow the specific binding of the label. As an example, a cysteine residue may be inserted at the desired position of the protein which inserts a thiol (SH) group that can be used to attach a label. The cysteine can either replace a natural occurring amino acid or can be incorporated as an addition amino acid. Care must be taken not to disrupt the biological function of the protein. A malemeide-activated label is then covalently attached to the thiol residue of the protein nanopore. In one embodiment, the attachment of the label to the protein nanopore or the label on the nucleic acid is reversible. By implementing a cleavable crosslinker, an easily breakable chemical bond (e.g. an S—S bond or a pH labile bond) is introduced and the label may be removed when the corresponding conditions are met.

A nanopore, or pore, may be labeled with one or more donor labels. For example, the cis side or surface and/or trans side or surface of the nanopore may be labeled with one or more donor labels. The label may be attached to the base of a pore or nanopore or to another portion or monomer making up the nanopore or pore A label may be attached to a portion of the membrane or substrate through which a nanopore spans or to a linker or other molecule attached to the membrane, substrate or nanopore. The nanopore or pore label may be positioned or attached on the nanopore, substrate or membrane such that the pore label can come into proximity with an acceptor label of a biological polymer, e.g., a nucleic acid, which is translocated through the pore. The donor labels may have the same or different emission or absorption spectra. The labeling of a pore structure may be achieved via covalent or non-covalent interactions.

A donor label may be placed as close as possible to the aperture of a nanopore without causing an occlusion that impairs translocation of a nucleic acid through the nanopore. A pore label may have a variety of suitable properties and/or characteristics. For example, a pore label may have energy absorption properties meeting particular requirements. A pore label may have a large radiation energy absorption cross-section, ranging, for example, from about 0 to 1000 nm or from about 200 to 500 nm. A pore label may absorb radiation within a specific energy range that is higher than the energy absorption of the nucleic acid label. The absorption energy of the pore label may be tuned with respect to the absorption energy of a nucleic acid label in order to control the distance at which energy transfer may occur between the two labels. A pore label may be stable and functional for at least $10^6$ or $10^9$ excitation and energy transfer cycles.

Treating Solid Phase Membranes to Reduce Autofluorescence

In some embodiments, a solid phase membrane of a microelectromechanical system (MEMS) material is treated with a low energy ion beam to bleach its autofluorescence. Typically such treatment is carried out by directing an ion beam to a surface region of the MEMS material, at a sufficiently high energy to cause a physical change in the MEMS material at its surface or near its surface to disrupt or inactivate structures contributing to autofluorescence, but not with such high energy that melting, vaporization, significant deformations or sputtering occur. The minimal energy required may be readily determined on a material-by-material basis by gradually increasing beam energy starting from zero and measuring reduction in autofluorescence with increasing beam energy. As used herein, the term "autofluorescence" is used synonymously with "background fluorescence" to mean fluorescence emanating from a source at or near a surface of a MEMS material upon excitation with a light source selected to excite a fluorescent label that is not a part of the MEMS material. Thus, autofluorescence in a MEMS material depends on the frequency of the light source. In one aspect, the frequency of the light source is selected to excite organic fluorescent dyes, so that the method reduces autofluorescence of frequencies in the visible range of light as well as frequencies from the near infrared to the near ultraviolet. MEMS materials include a wide variety of solids capable of microfabrication and use in analytical techniques using optical detection. Exemplary MEMS materials are silicon-based substrates, such as silicon nitride and silicon dioxide or metal based substrates, such as aluminum oxide. In one aspect, MEMS materials are processed and used in the form of a membrane. In one embodiment, the MEMS material is silicon nitride. A wide variety of focused ion beams may be employed for such bleaching and guidance for the production and application of such beams at various energies may be found in such references as, Natasi et al, Ion Solid Interactions: Fundamentals and Applications (Cambridge University Press, 1996), and like references. Exemplary focused ion beams include helium ion beams, neon ion beams and gallium ion beams. In one embodiment, a helium ion beam is used in the method. Helium ion beams may be produced with a commercially available ion beam microscope (HIM) (e.g. Zeiss Orion Nanofab). The amount of energy or dosage delivered to a surface of a MEMS material, such as silicon nitride, to reduce autofluorescence may be in the range of from 2e-10 to 8e-10 nC/nm^2.

Labels for Nanopores and Analytes

In some embodiments, a nanopore may be labeled with one or more quantum dots. In particular, in some embodiments, one or more quantum dots may be attached to a nanopore, or attached to a solid phase support adjacent to (and within a FRET distance of an entrance or exit of a nanopore), and employed as donors in FRET reactions with acceptors on analytes. Such uses of quantum dots are well known and are described widely in the scientific and patent literature, such as, in U.S. Pat. Nos. 6,252,303; 6,855,551; 7,235,361; and the like, which are incorporated herein by reference.

One example of a Quantum dot which may be utilized as a pore label is a CdTe quantum dot which can be synthesized in an aqueous solution. A CdTe quantum dot may be functionalized with a nucleophilic group such as primary amines, thiols or functional groups such as carboxylic acids. A CdTe quantum dot may include a mercaptopropionic acid capping ligand, which has a carboxylic acid functional group that may be utilized to covalently link a quantum dot to a primary amine on the exterior of a protein pore. The cross-linking reaction may be accomplished using standard cross-linking reagents (homo-bifunctional as well as hetero-bifunctional) which are known to those having ordinary skill in the art of bioconjugation. Care may be taken to ensure that the modifications do not impair or substantially impair the translocation of a nucleic acid through the nanopore. This may be achieved by varying the length of the employed crosslinker molecule used to attach the donor label to the nanopore.

The primary amine of the Lysin residue 131 of the natural alpha hemolysin protein (Song, L. et al., Science 274, (1996): 1859-1866) may be used to covalently bind carboxy modified CdTe Quantum dots via 1-Ethyl-3-[3-dimethylaminopropyl]carbodiimide hydrochloride/N-hydroxysulfosuccinimide (EDC/NHS) coupling chemistry. Alternatively, amino acid 129 (threonine) may be exchanged into cysteine. Since there is no other cysteine residue in the natural alpha hemolysin protein the thiol side group of the newly inserted cysteine may be used to covalently attach other chemical moieties.

A variety of methods, mechanisms and/or routes for attaching one or more pore labels to a pore protein may be utilized. A pore protein may be genetically engineered in a manner that introduces amino acids with known properties or various functional groups to the natural protein sequence. Such a modification of a naturally occurring protein sequence may be advantageous for the bioconjugation of Quantum dots to the pore protein. For example, the introduction of a cysteine residue would introduce a thiol group that would allow for the direct binding of a Quantum dot, such as a CdTe quantum dot, to a pore protein. Also, the introduction of a Lysin residue would introduce a primary amine for binding a Quantum dot. The introduction of glutamic acid or aspartic acid would introduce a carboxylic acid moiety for binding a Quantum dot. These groups are amenable for bioconjugation with a Quantum dot using either homo- or hetero-bifunctional crosslinker molecules. The insertions of poly-histidines allow the direct binding of Quantum dots to a protein pore via metal-histidine coordination. Such modifications to pore proteins aimed at the introduction of functional groups for bioconjugation are known to those having ordinary skill in the art. Care should be taken to ensure that the modifications do not impair or substantially impair the translocation of a nucleic acid through the nanopore.

The nanopore label can be attached to a protein nanopore before or after insertion of said nanopore into a lipid bilayer. Where a label is attached before insertion into a lipid bilayer, care may be taken to label the base of the nanopore and avoid random labeling of the pore protein. This can be achieved by genetic engineering of the pore protein to allow site specific attachment of the pore label (see section 0047). An advantage of this approach is the bulk production of labeled nanopores. Alternatively, a labeling reaction of a pre-inserted nanopore may ensure site-specific attachment of the label to the base (trans-side) of the nanopore without genetically engineering the pore protein.

A biological polymer, e.g., a nucleic acid molecule or polymer, may be labeled with one or more acceptor labels. For a nucleic acid molecule, each of the four nucleotides or building blocks of a nucleic acid molecule may be labeled with an acceptor label thereby creating a labeled (e.g., fluorescent) counterpart to each naturally occurring nucleotide. The acceptor label may be in the form of an energy accepting molecule which can be attached to one or more nucleotides on a portion or on the entire strand of a converted nucleic acid.

A variety of methods may be utilized to label the monomers or nucleotides of a nucleic acid molecule or polymer. A labeled nucleotide may be incorporated into a nucleic acid during synthesis of a new nucleic acid using the original sample as a template ("labeling by synthesis"). For example, the labeling of nucleic acid may be achieved via PCR, whole genome amplification, rolling circle amplification, primer extension or the like or via various combinations and extensions of the above methods known to persons having ordinary skill in the art.

Labeling of a nucleic acid may be achieved by replicating the nucleic acid in the presence of a modified nucleotide analog having a label, which leads to the incorporation of that label into the newly generated nucleic acid. The labeling process can also be achieved by incorporating a nucleotide analog with a functional group that can be used to covalently attach an energy accepting moiety in a secondary labeling step. Such replication can be accomplished by whole genome amplification (Zhang, L. et al., Proc. Natl. Acad. Sci. USA 89 (1992): 5847) or strand displacement amplification such as rolling circle amplification, nick translation, transcription, reverse transcription, primer extension and polymerase chain reaction (PCR), degenerate oligonucleotide primer PCR (DOP-PCR) (Telenius, H. et al., Genomics 13 (1992): 718-725) or combinations of the above methods.

A label may comprise a reactive group such as a nucleophile (amines, thiols etc.). Such nucleophiles, which are not present in natural nucleic acids, can then be used to attach fluorescent labels via amine or thiol reactive chemistry such as NHS esters, maleimides, epoxy rings, isocyanates etc. Such nucleophile reactive fluorescent dyes (i.e. NHS-dyes) are readily commercially available from different sources. An advantage of labeling a nucleic acid with small nucleophiles lies in the high efficiency of incorporation of such labeled nucleotides when a "labeling by synthesis" approach is used. Bulky fluorescently labeled nucleic acid building blocks may be poorly incorporated by polymerases due to steric hindrance of the labels during the polymerization process into newly synthesized DNA.

DNA can be directly chemically modified without polymerase mediated incorporation of labeled nucleotides. One example of a modification includes cis-platinum containing dyes that modify Guanine bases at their N7 position (Hoevel, T. et al., Bio Techniques 27 (1999): 1064-1067). Another example includes the modifying of pyrimidines with hydroxylamine at the C6 position which leads to 6-hydroxylamino derivatives. The resulting amine groups can be further modified with amine reactive dyes (e.g. NHS-Cy5). Yet another example are azide or alkyne modified nucleotides which are readily incorporated by polymerases (Gierlich et al., Chem. Eur. J., 2007, 13, 9486-0404). The alkyne or azide modified polynucleotide is subsequently labeled with an azide or alkyne modified fluorophore following well established click chemistry protocols.

A nucleic acid molecule may be directly modified with N-Bromosuccinimide which upon reacting with the nucleic acid will result in 5-Bromocystein, 8-Bromoadenine and 8-Bromoguanine. The modified nucleotides can be further reacted with di-amine nucleophiles. The remaining nucleophile can then be reacted with an amine reactive dye (e.g. NHS-dye) (Hermanson G. in Bioconjugate Techniques, Academic Press 1996, ISBN 978-0-12-342336-8).

A combination of 1, 2, 3 or 4 nucleotides in a nucleic acid strand may be exchanged with their labeled counterpart. The various combinations of labeled nucleotides can be sequenced in parallel, e.g., labeling a source nucleic acid or DNA with combinations of 2 labeled nucleotides in addition to the four single labeled samples, which will result in a total of 10 differently labeled sample nucleic acid molecules or DNAs (G, A, T, C, GA, GT, GC, AT, AC, TC). The resulting sequence pattern may allow for a more accurate sequence alignment due to overlapping nucleotide positions in the redundant sequence read-out.

In certain variations, a method for sequencing a polymer, such as a nucleic acid molecule, may include providing a nanopore or pore protein (or a synthetic pore) inserted in a membrane or membrane like structure or other substrate. The base or other portion of the pore may be modified with one or more pore labels. The base may refer to the Trans side of the pore. Optionally, the Cis and/or Trans side of the pore may be modified with one or more pore labels. Nucleic acid polymers to be analyzed or sequenced may be used as a template for producing a labeled version of the nucleic acid polymer, in which one of the four nucleotides or up to all four nucleotides in the resulting polymer is/are replaced with the nucleotide's labeled analogue(s). An electric field is applied to the nanopore which forces the labeled nucleic acid polymer through the nanopore, while an external monochromatic or other light source may be used to illuminate the nanopore, thereby exciting the pore label. As, after or before labeled nucleotides of the nucleic acid pass through, exit or enter the nanopore, energy is transferred from the pore label to a nucleotide label, which results in emission of lower energy radiation. The nucleotide label radiation is then detected by a confocal microscope setup or other optical detection system or light microscopy system capable of single molecule detection known to people having ordinary skill in the art. Examples of such detection systems include but are not limited to confocal microscopy, epifluorescent microscopy and total internal reflection fluorescent (TIRF) microscopy. Other polymers (e.g., proteins and polymers other than nucleic acids) having labeled monomers may also be sequenced according to the methods described herein.

Energy may be transferred from a pore or nanopore donor label (e.g., a Quantum Dot) to an acceptor label on a polymer (e.g., a nucleic acid) when an acceptor label of an acceptor labeled monomer (e.g., nucleotide) of the polymer interacts with the donor label as, after or before the labeled monomer exits, enters or passes through a nanopore. For example, the donor label may be positioned on or attached to the nanopore on the cis or trans side or surface of the nanopore such that the interaction or energy transfer between the donor label and acceptor label does not take place until the labeled monomer exits the nanopore and comes into the vicinity or proximity of the donor label outside of the nanopore channel or opening. As a result, interaction between the labels, energy transfer from the donor label to the acceptor label, emission of energy from the acceptor label and/or measurement or detection of an emission of energy from the acceptor label may take place outside of the passage, channel or opening running through the nanopore, e.g., within a cis or trans chamber on the cis or trans sides of a nanopore. The measurement or detection of the energy emitted from the acceptor label of a monomer may be utilized to identify the monomer.

The nanopore label may be positioned outside of the passage, channel or opening of the nanopore such that the label may be visible or exposed to facilitate excitation or illumination of the label. The interaction and energy transfer between a donor label and accepter label and the emission of energy from the acceptor label as a result of the energy transfer may take place outside of the passage, channel or opening of the nanopore. This may facilitate ease and accuracy of the detection or measurement of energy or light emission from the acceptor label, e.g., via an optical detection or measurement device. The donor and acceptor label interaction may take place within a channel of a nanopore and a donor label could be positioned within the channel of a nanopore.

A donor label may be attached in various manners and/or at various sites on a nanopore. For example, a donor label may be directly or indirectly attached or connected to a portion or unit of the nanopore. Alternatively, a donor label may be positioned adjacent to a nanopore.

Each acceptor labeled monomer (e.g., nucleotide) of a polymer (e.g., nucleic acid) can interact sequentially with a donor label positioned on or next to or attached directly or indirectly to a nanopore or channel through which the polymer is translocated. The interaction between the donor and acceptor labels may take place outside of the nanopore channel or opening, e.g., after the acceptor labeled monomer exits the nanopore or before the monomer enters the nanopore. The interaction may take place within or partially within the nanopore channel or opening, e.g., while the acceptor labeled monomer passes through, enters or exits the nanopore.

When one of the four nucleotides of a nucleic acid is labeled, the time dependent signal arising from the single nucleotide label emission is converted into a sequence corresponding to the positions of the labeled nucleotide in the nucleic acid sequence. The process is then repeated for each of the four nucleotides in separate samples and the four partial sequences are then aligned to assemble an entire nucleic acid sequence.

When multi-color labeled nucleic acid (DNA) sequences are analyzed, the energy transfer from one or more donor labels to each of the four distinct acceptor labels that may exist on a nucleic acid molecule may result in light emission at four distinct wavelengths or colors (each associated with one of the four nucleotides) which allows for a direct sequence read-out.

Translocation Speed

A major obstacle associated with Nanopore based sequencing approaches is the high translocation velocity of nucleic acid through a nanopore (~500,000-1,000,000 nucleotides/sec) which doesn't allow for direct sequence readout due to the limited bandwidth of the recording equipment. A way of slowing down the nucleic acid translocation with two different nanopore proteins was recently shown by Cherf et al. (Nat Biotechnol, 2012 Feb. 14; 30(4):344-8) and Manrao et al. (Nat Biotechnol. 2012 Mar. 25; 30(4):349-53) and are incorporated herein by reference. Both groups used a DNA polymerase to synthesize a complementary strand from a target template which resulted in the step-wise translocation of the template DNA through the nanopore. Hence, the synthesis speed of the nucleic acid polymerase (10-500 nucleotides/sec) determined the translocation speed of the DNA and since it's roughly 3-4 orders of magnitude slower than direct nucleic acid translocation the analysis of single nucleotides became feasible. However, the polymerase-aided translocation requires significant sample preparation to generate a binding site for the polymerase and the nucleic acid synthesis has to be blocked in bulk and can only start once the nucleic acid-polymerase complex is captured by the nanopore protein. This results in a rather complex set-up which might prevent the implementation in a commercial setting. Furthermore, fluctuation in polymerase synthesis reactions such as a stalled polymerization as well as the dissociation of the polymerase from the nucleic acid may hamper the sequence read-out resulting in a high error rate and reduced read-length, respectively. Optical Nanopore sequence as described in this application uses a different way of slowing down the DNA translocation. A target nucleic acid is enzymatically copied by incorporating fluorescent modified nucleotides. The resulting labeled nucleic acid has an increased nominal diameter which results in a decreased translocation velocity when pulled through a nanopore. The preferred translocation rate for optical sequencing lies in the range of 1-1000 nucleotides per second with a more preferred range of 200-800 nucleotides per second and a most preferred translocation rate of 200-600 nucleotides per second.

Alternatively, translocation speed of a polynucleotide, especially a single stranded polynucleotide, may be controlled by employing a nanopore dimensioned so that adducts and/or labels, e.g. organic dyes attached to bases, inhibit but do not prevent polynucleotide translocation. A translocation speed may be selected by attaching labels and/or adducts at a predetermined density. Such labels and/or adducts may have regular spaced attachments, e.g. every third nucleotide or the like, or they may have random, or pseudorandom attachments, e.g. every C may be labeled. In some embodiments, a selected number of different nucleotides may be labeled, e.g. every A and C, or every A and G, or every A and T, or every C, or the like, that results in an average translocation speed. Such average speed may be decreased by attaching adducts to unlabeled nucleotides. Adducts include any molecule, usually and organic molecule, that may be attached to a nucleotide using conventional chemistries. Typically adducts have a molecular weight in the same range as common organic dyes, e.g. fluorescein, Cy3, or the like. Adducts may or may not be capable of generating signals, that is, serving as a label. In some embodiments, adducts and/or labels are attached to bases of nucleotides. In other embodiments, labels and/or adducts may be attached to linkages between nucleosides in a polynucleotide. In one aspect, a method of controlling translocation velocity of a single stranded polynucleotide through a nanopore comprises the step of attaching adducts to the polynucleotide at a density, wherein translocation velocity of the single stranded polynucleotide monotonically decreases with a larger number of adducts attached, or with the density of adducts attached. In some embodiments, not every kind of nucleotide of a polynucleotide is labeled. For example, four different sets of a polynucleotide may be produced where nucleotides of each set are labeled with the same molecule, e.g. a fluorescent organic dye acceptor, but in each set a different kind of nucleotide will be labeled. Thus, in set 1 only A's may be labeled; in set 2 only C's may be labeled; in set 3 only G's may be labeled; and so on. After such labeling, the four sets of polynucleotides may then be analyzed separately in accordance with the methods and systems described herein and a nucleotide sequence of the polynucleotide determined from the data generated in the four analysis. In such embodiments, and similar embodiments, e.g. two labels are used, where some of the nucleotides of a polynucleotide are not labeled, translocation speed through a nanopore will be affected by the distribution of label along the polynucleotide. To prevent such variability in translocation speed, in some embodiments, nucleotides that are not labeled with an acceptor or donor for generating signals to determine nucleotide sequence, may be modified by attaching a non-signal-producing adduct that has substantially the same effect on translocation speed as the signal-producing labels.

Example

In this example, a nanopore apparatus is described for determining a sequence of acceptor-labeled nucleotides of a polynucleotide, after which it is used to detect a sequence of acceptor-labeled cytosines in a first polynucleotide and to detect a sequence of first acceptor-labeled thymines or thymidines and second acceptor-labeled cytosines in a second polynucleotide.

HIM drilling to form nanopore(s) in a silicon nitride membrane: A 3 mm Si chip (Protochips, NC) with a 50×50 um etched window spanned by a 30 nm $Si_3N_4$ membrane is cleaned with oxygen plasma prior to the drilling process. The cleaned chip is inserted into the vacuum chamber of a Helium Ion Microscope (Orion, Zeiss). After insertion, the nanoholes are drilled with a focused ion stream with a beam current of ~5 pA through a 20 um aperture and with an exposure time calibrated to result in 4+/−2 nm holes Protein nanopores: A cloned variant of the wt alpha hemolysin protein is used as a template for an in vitro transcription/translation reaction. The resulting monomers are heptamerized by a stepwise addition of sodium deoxycholate to a final concentration of 6.25 mM and a subsequent incubation for 12 hours at 4 C. The resulting heptamer is attached to an amine-modified oligonucleotide using a heterobifunctional crosslinker (SMCC, Sulfosuccinimidyl-4-(N-maleimidomethyl)cyclohexane-1-carboxylate). This oligonucleotide serves as a hybridization site for a 3 kb ds-DNA fragment which is used as a drag force to pull the protein nanopore into the drilled holes in the $Si_3N_4$ membrane. In addition to the oligonucleotide modification, the base of the protein nanopore is also modified with one or more maleimide activated fluorescent dyes. The attached fluorophores can either serve as donor or acceptor in a FRET reaction.

Hybrid Nanopore: TEM grids with drilled holes are cleaned by submersing in 90 C hot Piranha solution (3:1 Sulfuric acid:$H_2O_2$, v/v) for 15 min or by an air plasma for 5 min. After extensive rinsing with water the TEM grid is installed in a Delrin holder separating a cis and trans chamber. The trans chamber is sealed with a cover slip that allows the optical interrogation of the nanopores. Each chamber is filled with Ethanol to promote wetting of the nanopores. The Ethanol is subsequently exchanged with water and then a buffered 1 M KCl solution. In the trans chamber the buffered KCl contains 50% glycerol to facilitate TIR (total internal reflection) imaging. Both the cis and trans chamber harbor a Ag/AgCl electrode in contact with the buffer solution with the cathode (+) in the cis and the anode (−) in the trans chamber. The nanopore protein is added to the cis side of the SiN membrane and by applying an electric field (200-600 mV) the protein nanopore is plugged into the drilled nanoholes forming a hybrid nanopore.

After 5-25 min at 600 mV usually 50-75% of the drilled holes have a protein nanopore inserted. The formation of the hybrid nanopores is checked on an inverted microscope (Olympus IX71) equipped with an APON 60×TIRF oil-immersion objective and a 532 nm diode laser which is used to excite the fluorophore attached to the protein nanopore. The buffer in the cis chamber is exchanged to remove excess nanopore protein. Labeled single stranded (ss) DNA at a final concentration of 10 nM is added to the cis chamber. The electric field is reduced to 200-400 mV which promotes the translocation of ssDNA through the hybrid nanopore. The labeled DNA, when exiting the nanopore, comes in close proximity to the excited donor fluorophore. A FRET reaction occurs which results in the photon emission from the labeled DNA. Emitted photons are collected, filtered and imaged using an Orca Flash 4.0 cMOS camera (Hamamatsu) at a frame rate of 500-5000 Hz. Data is extracted from a 5×5 pixel area covering the entire hybrid nanopore from the raw tiff images using ImageJ. Raw traces are normalized and a peak find algorithm is used to identify FRET signal. Base calling is performed on the identified peaks.

Each cytosine of the following 107-mer single stranded polynucleotide (SEQ ID NO: 1) was labeled with a Cy5 fluorophore.

3'-AACGGCCCTTCGATCTCATTGAGGATGAGAGGAGAGTCAAAGGAAGA-

ACGAGGATGAGAGGAGAGTGAGAGCAAAGGAAGAACGAGGATGAGAGG-

AGAGTGAGAGCAAAGGAAGAA-5'

The labeled polynucleotide was translocated in a 3'-first orientation through the hybrid nanopore and mixed FRET signals from the labeled cytosines was collected. Raw data is shown in FIG. 1B. When translocated through the hybrid nanopore multiple peaks are observed which correspond to the number of cytosines in the DNA. Remarkably, the homopolymer at the 3' end is perfectly resolved.

After the 20$^{th}$ nucleotide position from the 5' end, every cytosine and every thymidine of the following single stranded polynucleotide (SEQ ID NO: 2) were labeled with Cy5 and Atto700, respectively.

5'-GCTATGTGGCGCGGTATTATTAAGAAGGAGACTGAGAGGAGAGAA-

GGAGCAAGAAGGAAATGAGAGCGAGAGGAGAGAAGGAGGAAGAAG-3'

Figure 1D:
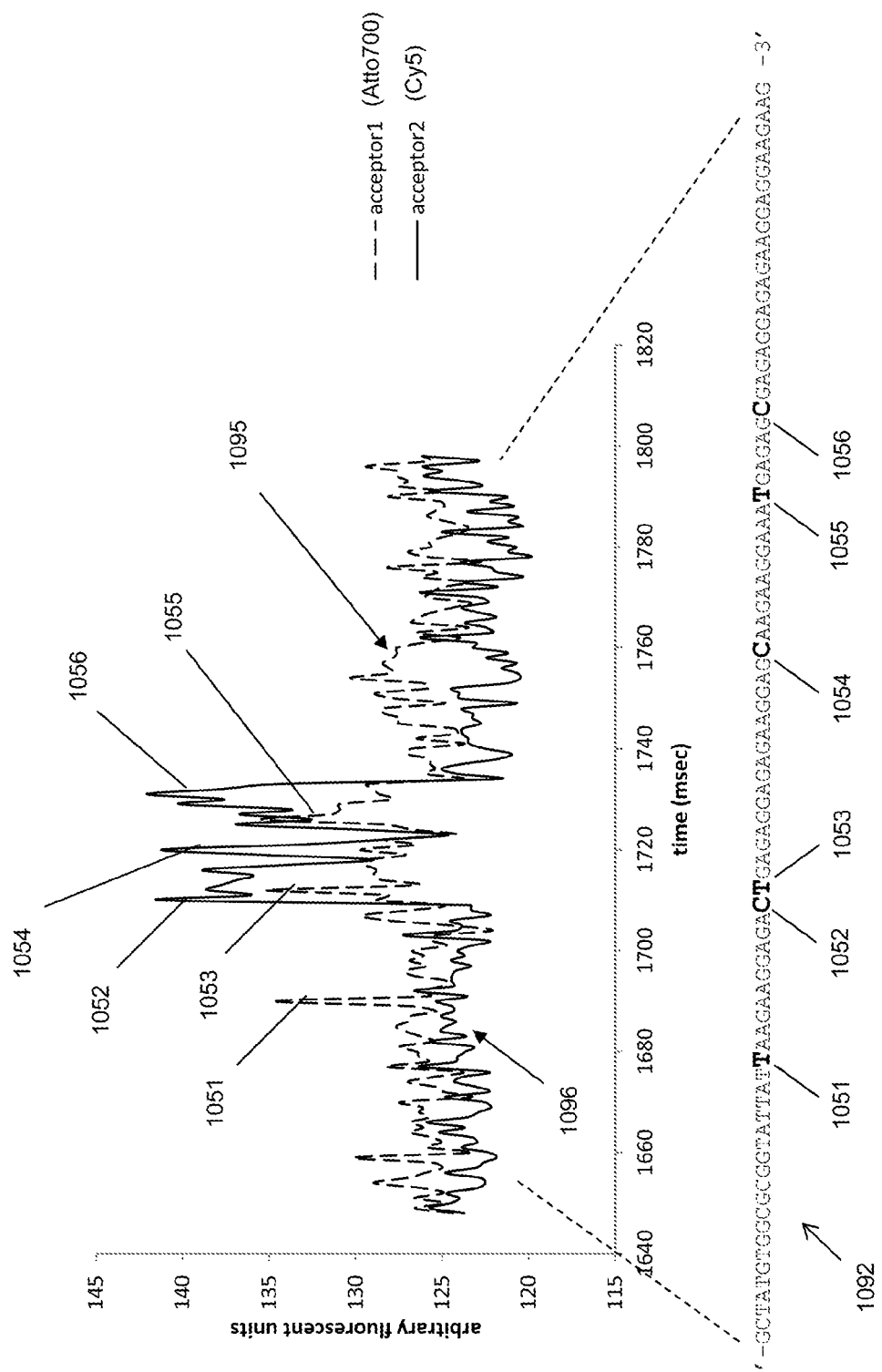
FIG. 1D shows data of mixed FRET signals of a test polynucleotide labeled with two kinds of acceptor molecules.

The labeled polynucleotide was translocated in a 3'-first orientation through the hybrid nanopore and mixed FRET signals from the labeled cytosines and thymidines were collected. Raw data is shown in FIG. 1D. The peaks in this raw data trace show a pattern that resembles the position of the labeled nucleotides in the template strand.

This disclosure is not intended to be limited to the scope of the particular forms set forth, but is intended to cover alternatives, modifications, and equivalents of the variations described herein. Further, the scope of the disclosure fully encompasses other variations that may become obvious to those skilled in the art in view of this disclosure. The scope of the present invention is limited only by the appended claims.

Definitions

"Nanopore" means any opening positioned in a substrate that allows the passage of analytes through the substrate in a predetermined or discernable order, or in the case of polymer analytes, passage of their monomeric units through the substrate in a predetermined or discernible order. In the latter case, a predetermined or discernible order may be the primary sequence of monomeric units in the polymer. Examples of nanopores include proteinaceous or protein based nanopores, synthetic or solid state nanopores, and hybrid nanopores comprising a solid state nanopore having a protein nanopore embedded therein. A nanopore may have an inner diameter of, e.g., 1-10 nm or 1-5 nm or 1-3 nm, or other various sizes. Examples of protein nanopores include but are not limited to, alpha-hemolysin, voltage-dependent mitochondrial porin (VDAC), OmpF, OmpC, MspA and LamB (maltoporin), e.g. disclosed in Rhee, M. et al., Trends in Biotechnology, 25 (4) (2007): 174-181; Bayley et al (cited above); Gundlach et al, U.S. patent publication 2012/0055792; and the like, which are incorporated herein by reference. Any protein pore that allows the translocation of single nucleic acid molecules may be employed. A nanopore protein may be labeled at a specific site on the exterior of the pore, or at a specific site on the exterior of one or more monomer units making up the pore forming protein. Pore proteins are chosen from a group of proteins such as, but not limited to, alpha-hemolysin, MspA, voltage-dependent mitochondrial porin (VDAC), Anthrax porin, OmpF, OmpC and LamB (maltoporin). Integration of the pore protein into a solid state hole is accomplished by attaching a charged polymer to the pore protein. After applying an electric field the charged complex is electrophoretically pulled into the solid state hole. A synthetic nanopore, or solid-state nanopore, may be created in various forms of solid substrates, examples of which include but are not limited to silicones (e.g. Si3N4, SiO2), metals, metal oxides (e.g. Al2O3) plastics, glass, semiconductor material, and combinations thereof. A synthetic nanopore may be more stable than a biological protein pore positioned in a lipid bilayer membrane. A synthetic nanopore may also be created by using a carbon nanotube embedded in a suitable substrate such as but not limited to polymerized epoxy. Carbon nanotubes can have uniform and well-defined chemical and structural properties. Various sized carbon nanotubes can be obtained, ranging from one to hundreds of nanometers. The surface charge of a carbon nanotube is known to be about zero, and as a result, electrophoretic transport of a nucleic acid through the nanopore becomes simple and predictable (Ito, T. et al., Chem. Commun. 12 (2003): 1482-83). The substrate surface of a synthetic nanopore may be chemically modified to allow for covalent attachment of the protein pore or to render the surface properties suitable for optical nanopore sequencing. Such surface modifications can be covalent or non-covalent. Most covalent modification include an organosilane deposition for which the most common protocols are described: 1) Deposition from aqueous alcohol. This is the most facile method for preparing silylated surfaces. A 95% ethanol-5% water solution is adjusted to pH 4.5-5.5 with acetic acid. Silane is added with stirring to yield a 2% final concentration. After hydrolysis and silanol group formation the substrate is added for 2-5 min. After rinsed free of excess materials by dipping briefly in ethanol. Cure of the silane layer is for 5-10 min at 110 degrees Celsius. 2) Vapor Phase Deposition. Silanes can be applied to substrates under dry aprotic conditions by chemical vapor deposition methods. These methods favor monolayer deposition. In closed chamber designs, substrates are heated to sufficient temperature to achieve 5 mm vapor pressure. Alternatively, vacuum can be applied until silane evaporation is observed. 3) Spin-on deposition. Spin-on applications can be made under hydrolytic conditions which favor maximum functionalization and polylayer deposition or dry conditions which favor monolayer deposition.

"FRET" or "Forrester, or fluorescence, resonant energy transfer" means a non-radiative dipole-dipole energy transfer mechanism from a donor to acceptor fluorophore. The efficiency of FRET may be dependent upon the distance between donor and acceptor as well as the properties of the fluorophores (Stryer, L., Annu Rev Biochem. 47 (1978): 819-846). "FRET distance" means a distance between a FRET donor and a FRET acceptor over which a FRET interaction can take place and a detectable FRET signal produced by the FRET acceptor.

"Polynucleotide" or "oligonucleotide" are used interchangeably and each mean a linear polymer of nucleotide monomers. Monomers making up polynucleotides and oligonucleotides are capable of specifically binding to a natural polynucleotide by way of a regular pattern of monomer-to-monomer interactions, such as Watson-Crick type of base pairing, base stacking, Hoogsteen or reverse Hoogsteen types of base pairing, or the like. Such monomers and their internucleosidic linkages may be naturally occurring or may be analogs thereof, e.g. naturally occurring or non-naturally occurring analogs. Non-naturally occurring analogs may include PNAs, phosphorothioate internucleosidic linkages, bases containing linking groups permitting the attachment of labels, such as fluorophores, or haptens, and the like. Whenever the use of an oligonucleotide or polynucleotide requires enzymatic processing, such as extension by a polymerase, ligation by a ligase, or the like, one of ordinary skill would understand that oligonucleotides or polynucleotides in those instances would not contain certain analogs of internucleosidic linkages, sugar moieties, or bases at any or some positions. Polynucleotides typically range in size from a couple or a few monomeric units, e.g. 5-40, when they are usually referred to as "oligonucleotides." to several thousand monomeric units. Whenever a polynucleotide or oligonucleotide is represented by a sequence of letters (upper or lower case), such as "ATGCCTG," it will be understood that the nucleotides are in $5'\rightarrow 3'$ order from left to right and that "A" denotes deoxyadenosine, "C" denotes deoxycytidine, "G" denotes deoxyguanosine, and "T" denotes thymidine, "I" denotes deoxyinosine, "U" denotes uridine, unless otherwise indicated or obvious from context. Unless otherwise noted the terminology and atom numbering conventions will follow those disclosed in Strachan and Read, Human Molecular Genetics 2 (Wiley-Liss, New York, 1999). Usually polynucleotides comprise the four natural nucleosides (e.g. deoxyadenosine, deoxycytidine, deoxyguanosine, deoxythymidine for DNA or their ribose counterparts for RNA) linked by phosphodiester linkages; however, they may also comprise non-natural nucleotide analogs, e.g. including modified bases, sugars, or internucleosidic linkages. It is clear to those skilled in the art that where an enzyme has specific oligonucleotide or polynucleotide substrate requirements for activity, e.g. single stranded DNA, RNA/DNA duplex, or the like, then selection of appropriate composition for the oligonucleotide or polynucleotide substrates is well within the knowledge of one of ordinary skill, especially with guidance from treatises, such as Sambrook et al, Molecular Cloning, Second Edition (Cold Spring Harbor Laboratory, New York, 1989), and like references. Likewise, the oligonucleotide and polynucleotide may refer to either a single stranded form or a double stranded form (i.e. duplexes of an oligonucleotide or polynucleotide and its respective complement). It will be clear to one of ordinary skill which form or whether both forms are intended from the context of the terms usage.

"Sequence determination", "sequencing" or "determining a nucleotide sequence" or like terms in reference to polynucleotides includes determination of partial as well as full sequence information of the polynucleotide. That is, the terms include sequences of subsets of the full set of four natural nucleotides, A, C, G and T, such as, for example, a sequence of just A's and C's of a target polynucleotide. That is, the terms include the determination of the identities, ordering, and locations of one, two, three or all of the four types of nucleotides within a target polynucleotide. In some embodiments, the terms include the determination of the identities, ordering, and locations of two, three or all of the four types of nucleotides within a target polynucleotide. In some embodiments sequence determination may be accomplished by identifying the ordering and locations of a single type of nucleotide, e.g. cytosines, within the target polynucleotide "catcgc . . . " so that its sequence is represented as a binary code, e.g. "100101 . . . " representing "c-(not c)not c)c-(not c)-c . . . " and the like. In some embodiments, the terms may also include subsequences of a target polynucleotide that serve as a fingerprint for the target polynucleotide; that is, subsequences that uniquely identify a target polynucleotide within a set of polynucleotides, e.g. all different RNA sequences expressed by a cell.

Each of the individual variations and embodiments described and illustrated herein has discrete components and features which may be readily separated from or combined with the features of any of the other variations. Modifications may be made to adapt a particular situation, material, composition of matter, process, process act(s) or step(s) to the objective(s), spirit or scope of the present invention.

Methods recited herein may be carried out in any order of the recited events which is logically possible, as well as the recited order of events. Furthermore, where a range of values is provided, every intervening value between the upper and lower limit of that range and any other stated or intervening value in that stated range is encompassed within the invention. Also, any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise, all technical and scientific terms used herein have the same meaning as commonly understood by one of ordinary skill in the art to which this invention belongs.

This disclosure is not intended to be limited to the scope of the particular forms set forth, but is intended to cover alternatives, modifications, combinations of elements disclosed in different variations, and equivalents of the variations described herein. Further, the scope of the disclosure fully encompasses other variations that may become obvious to those skilled in the art in view of this disclosure. The scope of the present invention is limited only by the appended claims.

What is claimed is:

1. A method of determining a nucleotide sequence of a polynucleotide, the method comprising the steps of: translocating a polynucleotide through a nanopore so that nucleotides of the polynucleotide pass in sequence by a FRET donor positioned adjacent to the nanopore, a plurality of the nucleotides being within a FRET distance of the FRET donor as the nucleotides exit the nanopore and at least a portion of the nucleotides being labeled with a FRET acceptor, the nanopore dimensioned so that acceptor labels on the nucleotides inside the nanopore are constrained to suppress FRET reactions and wherein different kinds of nucleotides are labeled with FRET acceptors that generate distinguishable signals;
    exciting the FRET donor adjacent to the nanopore so that FRET occurs between the FRET donor and a plurality of FRET acceptors on the plurality of nucleotides emerging from the nanopore and within the FRET distance to generate a mixed FRET signal;
    measuring the mixed FRET signals within the FRET distance as the polynucleotide translocates through the nanopore;
    separating the distinguishable signals from the mixed FRET signal of each measurement; and
    determining a nucleotide sequence of the polynucleotide from the measured distinguishable signals separated from the mixed FRET signals collected from every nucleotide of the polynucleotide.

2. The method of claim 1, wherein said nanopore is disposed in a solid phase membrane and wherein said FRET donor is attached to the solid phase membrane adjacent to said nanopore.

3. The method of claim 1, wherein said nanopore is a protein nanopore and wherein said FRET donor is attached to the protein nanopore.

4. The method of claim 1, wherein the polynucleotide is a single stranded polynucleotide.

5. The method of claim 1, wherein said step of exciting said FRET donor includes exposing said FRET donor to an illumination beam.

6. A method of determining a nucleotide sequence of a polynucleotide, the method comprising the steps of: translocating a polynucleotide through a nanopore having an exit so that nucleotides of the polynucleotide pass in sequence through a FRET zone upon exiting the nanopore, the FRET zone encompassing a plurality of the nucleotides during such passage and at least a portion of the nucleotides being labeled with FRET acceptors and at least one FRET donor being in the FRET zone, the nanopore dimensioned so that acceptor labels on the nucleotides inside the nanopore are constrained to suppress FRET reactions and wherein different kinds of nucleotides are labeled with FRET acceptors that generate distinguishable signals;
    exciting the FRET donor in the FRET zone so that FRET occurs between the FRET donor and a plurality of FRET acceptors on the plurality of nucleotides emerging from the nanopore and in the FRET zone to generate a mixed FRET signal;
    measuring the mixed FRET signals within the FRET zone as the polynucleotide moves through the FRET zone;
    separating the distinguishable signals from the mixed FRET signal of each measurement; and determining a nucleotide sequence of the polynucleotide from the measured distinguishable signals separated from the mixed FRET signals collected from every nucleotide of the polynucleotide.

7. The method of claim 6, wherein said nanopore is disposed in a solid phase membrane and wherein said FRET donor is attached to the solid phase membrane adjacent to said nanopore.

8. The method of claim 6, wherein said nanopore is a protein nanopore and wherein said FRET donor is attached to the protein nanopore.

9. The method of claim 6, wherein the polynucleotide is a single stranded polynucleotide.

10. The method of claim 6, wherein said step of exciting said FRET donor includes exposing said FRET donor to an illumination beam.

11. A method of determining a nucleotide sequence of a polynucleotide, the method comprising the steps of: translocating a polynucleotide with acceptor-labeled nucleotides through a nanopore dimensioned so that acceptor labels on the nucleotides inside the nanopore are constrained to suppress FRET reactions, wherein nucleotides of the polynucleotide pass in sequence through a FRET zone of a FRET donor upon exiting the nanopore, wherein the FRET zone encompasses a plurality of the nucleotides during such passage, and wherein different kinds of nucleotides are labeled with acceptors that generate distinguishable signals;
    exciting the FRET donor in the FRET zone so that FRET occurs between the plurality of acceptor-labeled nucleotides in the FRET zone and the FRET donor to generate a mixed FRET signal;
    measuring the mixed FRET signals within the FRET zone as the polynucleotide moves through the FRET zone;
    separating the distinguishable signals from the mixed FRET signal of each measurement; and determining a nucleotide sequence of the polynucleotide from the measured distinguishable signals separated from the mixed FRET signals collected from every nucleotide of the polynucleotide.

12. The method of claim 11, wherein said nanopore is disposed in a solid phase membrane and wherein FRET donor is attached to the solid phase membrane adjacent to said nanopore.

13. The method of claim 11, wherein said nanopore is a protein nanopore and wherein said FRET donor is attached to the protein nanopore.

14. The method of claim 11, wherein the polynucleotide is a single stranded polynucleotide.

15. The method of claim 11, wherein at least one of said acceptors is a fluorescent organic dye.

16. The method of claim 11, wherein said FRET donor is a quantum dot.

17. The method of claim 11, wherein said step of exciting said FRET donor includes exposing said FRET donor to an illumination beam.

* * * * *